(12) United States Patent
Brotherton-Pleiss et al.

(10) Patent No.: US 9,499,548 B2
(45) Date of Patent: Nov. 22, 2016

(54) INHIBITORS OF BRUTON'S TYROSINE KINASE

(71) Applicant: Hoffmann-La Roche Inc., Nutley, NJ (US)

(72) Inventors: Christine E. Brotherton-Pleiss, Sunnyvale, CA (US); Ramona Hilgenkamp, Montclair, NJ (US); Rama K. Kondru, Morris Plains, NJ (US); Francisco Javier Lopez-Tapia, Honolulu, HI (US); Yan Lou, Pleasanton, CA (US)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/427,501

(22) PCT Filed: Sep. 10, 2013

(86) PCT No.: PCT/EP2013/068659
§ 371 (c)(1),
(2) Date: Mar. 11, 2015

(87) PCT Pub. No.: WO2014/040965
PCT Pub. Date: Mar. 20, 2014

(65) Prior Publication Data
US 2015/0210704 A1    Jul. 30, 2015

Related U.S. Application Data

(60) Provisional application No. 61/700,373, filed on Sep. 13, 2012.

(51) Int. Cl.
*C07D 487/04* (2006.01)
*C07D 401/14* (2006.01)
*C07D 413/14* (2006.01)
*C07D 403/14* (2006.01)
*C07D 405/14* (2006.01)

(52) U.S. Cl.
CPC .......... *C07D 487/04* (2013.01); *C07D 401/14* (2013.01); *C07D 403/14* (2013.01); *C07D 405/14* (2013.01); *C07D 413/14* (2013.01)

(58) Field of Classification Search
CPC . C07D 487/04; C07D 401/14; C07D 405/14
See application file for complete search history.

(56) References Cited

U.S. PATENT DOCUMENTS 8,940,741 B2 *   1/2015   Berthel ............... C07D 401/14
                                                              514/247

\* cited by examiner

*Primary Examiner* — Paul V Ward

(57) ABSTRACT

This application discloses compounds according to generic Formula I: wherein all variables are defined as described herein, which inhibit Btk. The compounds disclosed herein are useful to modulate the activity of Btk and treat diseases associated with excessive Btk activity. The compounds are further useful to treat inflammatory and auto immune diseases associated with aberrant B-cell proliferation such as rheumatoid arthritis. Also disclosed are compositions containing compounds of Formula I and at least one carrier, diluent or excipient.

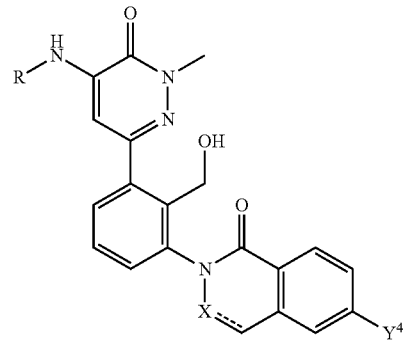

17 Claims, No Drawings

INHIBITORS OF BRUTON'S TYROSINE KINASE

This application is a National Stage Application of PCT/EP2013/068659, filed Sep. 10, 2013, which claims priority from Provisional Patent Application No. 61/700,373 filed on Sep. 13, 2012. Each of these applications is hereby incorporated by reference herein in its entirety.

FIELD OF THE INVENTION

The present invention relates to the use of novel compounds which inhibit Btk and are useful for the treatment of auto-immune and inflammatory diseases caused by aberrant B-cell activation.

BACKGROUND OF THE INVENTION

Protein kinases constitute one of the largest families of human enzymes and regulate many different signaling processes by adding phosphate groups to proteins (T. Hunter, Cell 1987 50:823-829). Specifically, tyrosine kinases phosphorylate proteins on the phenolic moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a target to modulate cellular function with small molecular kinase inhibitors and thus make good drug design targets. In addition to treatment of kinase-mediated disease processes, selective and efficacious inhibitors of kinase activity are also useful for investigation of cell signaling processes and identification of other cellular targets of therapeutic interest.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. Annu Rev Med 2004 55:477). Therefore inhibitors of the protein kinases that play a role in B-cell activation should be useful therapeutics for B-cell mediated disease pathology such as autoantibody production.

Signaling through the B-cell receptor (BCR) controls a range of B-cell responses including proliferation and differentiation into mature antibody producing cells. The BCR is a key regulatory point for B-cell activity and aberrant signaling can cause deregulated B-cell proliferation and formation of pathogenic autoantibodies that lead to multiple autoimmune and/or inflammatory diseases. Bruton's Tyrosine Kinase (Btk) is a non-BCR associated kinase that is membrane proximal and immediately downstream from BCR. Lack of Btk has been shown to block BCR signaling and therefore inhibition of Btk could be a useful therapeutic approach to block B-cell mediated disease processes.

Btk is a member of the Tec family of tyrosine kinases, and has been shown to be a critical regulator of early B-cell development and mature B-cell activation and survival (Khan et al. Immunity 1995 3:283; Ellmeier et al. J. Exp. Med. 2000 192:1611). Mutation of Btk in humans leads to the condition X-linked agammaglobulinemia (XLA) (reviewed in Rosen et al. New Eng. J. Med. 1995 333:431 and Lindvall et al. Immunol. Rev. 2005 203:200). These patients are immunocompromised and show impaired maturation of B-cells, decreased immunoglobulin and peripheral B-cell levels, diminished T-cell independent immune responses as well as attenuated calcium mobilization following BCR stimulation.

Evidence for a role for Btk in autoimmune and inflammatory diseases has also been provided by Btk-deficient mouse models. In preclinical murine models of systemic lupus erythematosus (SLE), Btk-deficient mice show marked amelioration of disease progression. In addition, Btk-deficient mice are resistant to collagen-induced arthritis (Jansson and Holmdahl Clin. Exp. Immunol. 1993 94:459). A selective Btk inhibitor has been demonstrated dose-dependent efficacy in a mouse arthritis model (Z. Pan et al., Chem. Med Chem. 2007 2:58-61).

Btk is also expressed by cells other than B-cells that may be involved in disease processes. For example, Btk is expressed by mast cells and Btk-deficient bone marrow derived mast cells demonstrate impaired antigen induced degranulation (Iwaki et al. J. Biol. Chem. 2005 280:40261). This shows Btk could be useful to treat pathological mast cells responses such as allergy and asthma. Also monocytes from XLA patients, in which Btk activity is absent, show decreased TNF alpha production following stimulation (Horwood et al. J Exp Med 197:1603, 2003). Therefore TNF alpha mediated inflammation could be modulated by small molecular Btk inhibitors. Also, Btk has been reported to play a role in apoptosis (Islam and Smith Immunol. Rev. 2000 178:49) and thus Btk inhibitors would be useful for the treatment of certain B-cell lymphomas and leukemias (Feldhahn et al. J. Exp. Med. 2005 201:1837).

SUMMARY OF THE INVENTION

The present application provides the Btk inhibitor compounds of Formula I, methods of use thereof, as described herein below:

The application provides a compound of Formula I,

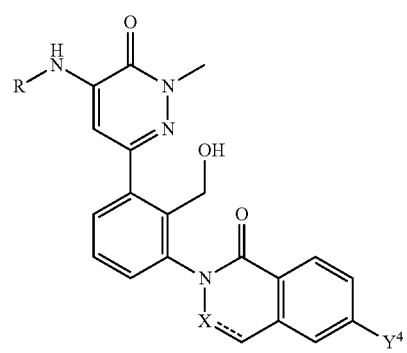

wherein:
$\rightleftharpoons$ is either a single or double bond;
X is either CH, $CH_2$, or N;
R is H, —$R^1$, —$R^1$—$R^2$—$R^3$, —$R^1$—$R^3$, or —$R^2$—$R^3$;
$R^1$ is aryl, heteroaryl, bicyclic heteroaryl, cycloalkyl, or heterocycloalkyl, each of which is optionally substituted with one or more lower alkyl, hydroxy, hydroxy lower alkyl, lower alkoxy, halo, nitro, amino, amido, cyano, oxo, or lower haloalkyl;
$R^2$ is —C(=O), —C(=O)O, —C(=O)$NR^{2'}$, —NHC(=O)O, —C($R^{2'}$)$_2$, —O, —S, —C(=NH)$NR^{2'}$, or —S(=O)$_2$;
each $R^{2'}$ is independently H or lower alkyl;
$R^3$ is H or $R^4$;

R⁴ is lower alkyl, lower haloalkyl, lower alkoxy, amino, lower alkyl amino, cycloalkyl amino, lower dialkyl amino, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, heterocycloalkyl alkyl, bicyclic cycloalkyl, bicyclic heterocycloalkyl, spirocycloalkyl, spiroheterocycloalkyl, or bicyclic spiroheterocycloalkyl, each of which is optionally substituted with one or more lower alkyl, halo, lower alkyl amino, lower dialkyl amino, hydroxy, hydroxy lower alkyl, lower alkoxy, lower alkanoyl, halo, nitro, amino, amido, acyl, cyano, oxo, sulfonyl, lower alkyl sulfonyl, guanidino, hydroxyl amino, carboxy, carbamoyl, carbamate, halo lower alkoxy, heterocycloalkyl, or halo lower alkyl, wherein two lower alkyl groups may together form a ring;

$Y^4$ is $Y^{4a}$, $Y^{4b}$, $Y^{4c}$, or $Y^{4d}$;

$Y^{4a}$ is H or halogen;

$Y^{4b}$ is lower alkyl, optionally substituted with one or more substituents selected from the group consisting of lower haloalkyl, halogen, hydroxy, amino, cyano, and lower alkoxy;

$Y^{4c}$ is lower cycloalkyl, optionally substituted with one or more substituents selected from the group consisting of lower alkyl, lower haloalkyl, halogen, hydroxy, amino, cyano, and lower alkoxy; and $Y^{4d}$ is amino, optionally substituted with one or more lower alkyl, alkoxy lower alkyl, or hydroxy lower alkyl;

or a pharmaceutically acceptable salt thereof.

The application provides a method for treating an inflammatory and/or autoimmune condition comprising administering to a patient in need thereof a therapeutically effective amount of the compound of Formula I.

The application provides a pharmaceutical composition comprising the compound of Formula I, admixed with at least one pharmaceutically acceptable carrier, excipient or diluent.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "-----" drawn through a bond each refer to the point of attachment of a functional group or other chemical moiety to the rest of the molecule of which it is a part. Thus, for example:

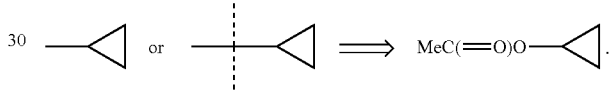

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds of Formulae I may exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl", "haloalkylheteroaryl", "arylalkylheterocyclyl", "alkylcarbonyl", "alkoxyalkyl," and the like. When the term "alkyl" is used as a suffix following another term, as in "phenylalkyl" or "hydroxyalkyl", this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "spirocycloalkyl", as used herein, means a spirocyclic cycloalkyl group, such as, for example, spiro [3.3]heptane. The term spiroheterocycloalkyl, as used herein, means a spirocyclic heterocycloalkyl, such as, for example, 2,6-diaza spiro[3.3]heptane.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl" or "hydroxyalkyl" this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo-lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethylethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "PCy$_3$" refers to a phosphine trisubstituted with three cyclic moieties.

The terms "haloalkoxy" or "halo-lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is/are replaced by hydroxyl groups.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The terms "alkylsulfonylamino" and "arylsulfonylamino" as used herein refers to a group of formula —NR'S(=O)$_2$R wherein R is alkyl or aryl respectively, R' is hydrogen or $C_{1-3}$ alkyl, and alkyl and aryl are as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "carboxy-alkyl" as used herein refers to an alkyl moiety wherein one, hydrogen atom has been replaced with a carboxyl with the understanding that the point of attachment of the heteroalkyl radical is through a carbon atom. The term "carboxy" or "carboxyl" refers to a —CO$_2$H moiety.

The term "heteroaryl" or "heteroaromatic" as used herein means a monocyclic or bicyclic radical of 5 to 12 ring atoms having at least one aromatic or partially unsaturated ring containing four to eight atoms per ring, incorporating one or more N, O, or S heteroatoms, the remaining ring atoms being carbon, with the understanding that the attachment point of the heteroaryl radical will be on an aromatic or partially unsaturated ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, oxazinyl, pyrrolyl, pyrazolyl, imidazolyl, oxazolyl, 4,5-Dihydro-oxazolyl, 5,6-Dihydro-4H-[1,3]oxazolyl, isoxazole, thiazole, isothiazole, triazoline, thiadiazole and oxadiazoline which can optionally be substituted with one or more, preferably one or two substituents selected from hydroxy, cyano, alkyl, alkoxy, thio, lower haloalkoxy, alkylthio, halo, lower haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole, naphthyridinyl, 5,6,7,8-Tetrahydro-[1,6]naphthyridinyl, and benzisothiazole. Bicyclic moieties can be optionally substituted on either ring, however the point of attachment is on a ring containing a heteroatom.

The term "heterocyclyl", "heterocycloalkyl" or "heterocycle" as used herein denotes a monovalent saturated cyclic radical, consisting of one or more rings, preferably one to two rings, including spirocyclic ring systems, of three to eight atoms per ring, incorporating one or more ring heteroatoms (chosen from N,O or S(O)$_{0-2}$), and which can optionally be independently substituted with one or more, preferably one or two substituents selected from hydroxy, oxo, cyano, lower alkyl, lower alkoxy, lower haloalkoxy, alkylthio, halo, lower haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and ionic forms thereof, unless otherwise indicated. Examples of heterocyclic radicals include, but are not limited to, morpholinyl, piperazinyl, piperidinyl, azetidinyl, pyrrolidinyl, hexahydroazepinyl, oxetanyl, tetrahydrofuranyl, tetrahydrothiophenyl, oxazolidinyl, thiazolidinyl, isoxazolidinyl, tetrahydropyranyl, thiomorpholinyl, quinuclidinyl and imidazolinyl, and ionic forms thereof. Examples may also be bicyclic, such as, for example, 3,8-diaza-bicyclo[3.2.1]octane, 2,5-diaza-bicyclo[2.2.2]octane, or octahydro-pyrazino[2,1-c][1,4]oxazine.

Inhibitors of Btk

The application provides a compound of Formula I,

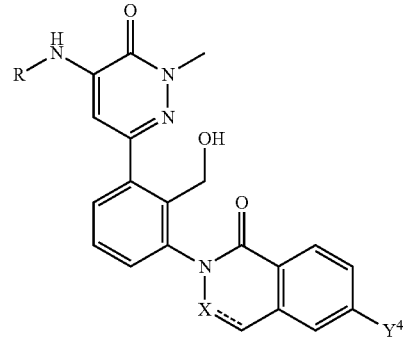

I wherein:
≡ is either a single or double bond;
X is either CH, CH$_2$, or N;
R is H, —R$^1$, —R$^1$—R$^2$—R$^3$, —R$^1$—R$^3$, or —R$^2$—R$^3$;
R$^1$ is aryl, heteroaryl, bicyclic heteroaryl, cycloalkyl, or heterocycloalkyl, each of which is optionally substituted with one or more lower alkyl, hydroxy, hydroxy lower alkyl, lower alkoxy, halo, nitro, amino, amido, cyano, oxo, or lower haloalkyl;
R$^2$ is —C(=O), —C(=O)O, —C(=O)NR$^{2'}$, —NHC(=O)O, —C(R$^{2'}$)$_2$, —O, —S, —C(=NH)NR$^{2'}$, or —S(=O)$_2$;
each R$^{2'}$ is independently H or lower alkyl;
R$^3$ is H or R$^4$;
R$^4$ is lower alkyl, lower haloalkyl, lower alkoxy, amino, lower alkyl amino, cycloalkyl amino, lower dialkyl amino, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, heterocycloalkyl alkyl, bicyclic cycloalkyl, bicyclic heterocycloalkyl, spirocycloalkyl, spiroheterocycloalkyl, or bicyclic spiroheterocycloalkyl, each of which is optionally substituted with one or more lower alkyl, halo, lower alkyl amino, lower dialkyl amino, hydroxy, hydroxy lower alkyl, lower alkoxy, lower alkanoyl, halo, nitro, amino, amido, acyl, cyano, oxo, sulfonyl, lower alkyl sulfonyl, guanidino, hydroxyl amino, carboxy, carbamoyl, carbamate, halo lower alkoxy, heterocycloalkyl, or halo lower alkyl, wherein two lower alkyl groups may together form a ring;
Y$^4$ is Y$^{4a}$, Y$^{4b}$, Y$^{4c}$, or Y$^{4d}$;
Y$^{4a}$ is H or halogen;
Y$^{4b}$ is lower alkyl, optionally substituted with one or more substituents selected from the group consisting of lower haloalkyl, halogen, hydroxy, amino, cyano, and lower alkoxy;
Y$^{4c}$ is lower cycloalkyl, optionally substituted with one or more substituents selected from the group consisting of lower alkyl, lower haloalkyl, halogen, hydroxy, amino, cyano, and lower alkoxy; and
Y$^{4d}$ is amino, optionally substituted with one or more lower alkyl, alkoxy lower alkyl, or hydroxy lower alkyl;
or a pharmaceutically acceptable salt thereof.

Further it is to be understood that every embodiment relating to a specific residue R, R$^1$, R$^2$, R$^3$, R$^4$, X, R$^{2'}$ and Y$^4$ as disclosed herein may be combined with any other embodiment relating to another residue R, R$^1$, R$^2$, R$^3$, R$^4$, X, R$^{2'}$ and Y$^4$ as disclosed herein.

The application provides a compound of Formula I, wherein
═ is a double bond; and
X is N.

The application provides a compound of Formula I, wherein
═ is a single bond; and
X is $CH_2$.

The application provides a compound of Formula I, wherein
═ is a double bond;
X is N;
R is —$R^1$—$R^2$—$R^3$;
$R^1$ is pyridyl;
$R^2$ is —S(═O)$_2$,
$R^3$ is $R^4$; and
$R^4$ is lower alkyl.

The application provides a compound of Formula I, wherein
═ is a double bond;
X is N;
R is —$R^1$—$R^2$—$R^3$;
$R^1$ is pyridyl;
$R^2$ is —C(CH$_3$)$_2$;
$R^3$ is $R^4$; and
$R^4$ is lower alkyl amino, lower dialkyl amino, or heterocycloalkyl optionally substituted with one or more lower alkyl.

The application provides a compound of Formula I, wherein
═ is a double bond;
X is N;
R is —$R^1$—$R^2$—$R^3$;
$R^1$ is phenyl or pyridyl;
$R^2$ is —C(═O);
$R^3$ is $R^4$; and
$R^4$ is morpholine or piperazine, optionally substituted with one or more lower alkyl.

The application provides a compound of Formula I, wherein
═ is a double bond;
X is N; and
$Y^4$ is tert-butyl.

The application provides a compound of Formula I, wherein
═ is a double bond;
X is CH; and
$Y^4$ is

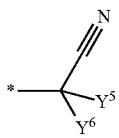

wherein, $Y^5$ and $Y^6$ are independently H, lower alkyl, or lower haloalkyl.

The application provides a compound of Formula I, wherein
═ is a double bond;
X is N; and
$Y^4$ is

wherein, $Y^5$ is H, halogen, lower alkyl or lower haloalkyl.

The application provides a compound of Formula I, wherein
═ is a double bond;
X is N; and
$Y^4$ is

wherein, $Y^5$ and $Y^6$ are independently H or lower alkyl.

The application provides a compound of Formula I, wherein
═ is a double bond;
X is N;
$Y^4$ is tert-butyl;
R is —$R^1$—$R^3$;
$R^1$ is pyridyl or pyrazolopyrazine;
$R^3$ is $R^4$; and
$R^4$ is optionally substituted lower alkyl, heterocycloalkyl, or alkyl heterocycloalkyl.

The application provides a compound of Formula I, wherein
═ is a double bond;
X is N;
$Y^4$ is tert-butyl;
R is —$R^1$—$R^2$—$R^3$;
$R^1$ is pyridyl;
$R^2$ is —C(CH$_3$)$_2$;
$R^3$ is $R^4$; and
$R^4$ is lower alkyl amino, lower dialkyl amino, or heterocycloalkyl optionally substituted with one or more lower alkyl.

The application provides a compound of Formula I, wherein
═ is a double bond;
X is N;
$Y^4$ is tert-butyl;
R is —$R^1$—$R^2$—$R^3$;
$R^1$ is pyridyl;
$R^2$ is —C(═O);
$R^3$ is $R^4$; and
$R^4$ is optionally substituted heterocycloalkyl or bicyclic spiroheterocycloalkyl.

The application provides a compound of Formula I, wherein
═ is a double bond;
X is N;
$Y^4$ is tert-butyl;
R is —$R^1$—$R^2$—$R^3$;
$R^1$ is pyridyl;
$R^2$ is —C(═O);
$R^3$ is $R^4$; and
$R^4$ is optionally substituted morpholine or piperazine.

The application provides a compound of Formula I selected from the group consisting of:

2-(3-{5-[5-(2-Azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-6-tert-butyl-2H-phthalazin-1-one;

6-tert-Butyl-2-{2-hydroxymethyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-2H-phthalazin-1-one;

2-{3-[5-(5-Azetidin-1-ylmethyl-1-methyl-1H-pyrazol-3-ylamino)-1-methyl-6-oxo-1,6-dihydro-pyridazin-3-yl]-2-hydroxymethyl-phenyl}-6-tert-butyl-2H-phthalazin-1-one;

6-tert-Butyl-2-(2-hydroxymethyl-3-{1-methyl-5-[5-((S)-1-methyl-pyrrolidin-2-yl)-pyridin-2-ylamino]-6-oxo-1,6-dihydro-pyridazin-3-yl}-phenyl)-2H-phthalazin-1-one;

6-tert-Butyl-2-(2-hydroxymethyl-3-{1-methyl-5-[5-((S)-1-methyl-pyrrolidin-3-yl)-pyridin-2-ylamino]-6-oxo-1,6-dihydro-pyridazin-3-yl}-phenyl)-2H-phthalazin-1-one;

6-tert-Butyl-2-(2-hydroxymethyl-3-{1-methyl-5-[5-((R)-1-methyl-pyrrolidin-3-yl)-pyridin-2-ylamino]-6-oxo-1,6-dihydro-pyridazin-3-yl}-phenyl)-2H-phthalazin-1-one;

2-(2-{2-Hydroxymethyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-1-oxo-1,2-dihydro-phthalazin-6-yl)-2-methyl-propionitrile;

6-tert-Butyl-2-{2-hydroxymethyl-3-[1-methyl-5-(5-methyl-4,5,6,7-tetrahydro-pyrazolo[1,5-a]pyrazin-2-ylamino)-6-oxo-1,6-dihydro-pyridazin-3-yl]-phenyl}-2H-phthalazin-1-one;

6-tert-Butyl-2-{3-[5-(1'-ethyl-1',2',3',4',5',6'-hexahydro-[3,4']bipyridinyl-6-ylamino)-1-methyl-6-oxo-1,6-dihydro-pyridazin-3-yl]-2-hydroxymethyl-phenyl}-2H-phthalazin-1-one;

6-tert-Butyl-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-2H-phthalazin-1-one;

2-[2-(3-{5-[5-(2-Azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-1-oxo-1,2-dihydro-phthalazin-6-yl]-2-methyl-propionitrile;

6-tert-Butyl-2-[2-hydroxymethyl-3-(5-{5-[2-(3-hydroxy-propylamino)-1,1-dimethyl-ethoxy]-pyridin-2-ylamino}-1-methyl-6-oxo-1,6-dihydro-pyridazin-3-yl)-phenyl]-2H-phthalazin-1-one;

6-tert-Butyl-2-{2-hydroxymethyl-3-[1-methyl-5-(1'-oxetan-3-yl-1',2',3',4',5',6'-hexahydro-[3,4']bipyridinyl-6-ylamino)-6-oxo-1,6-dihydro-pyridazin-3-yl]-phenyl}-2H-phthalazin-1-one;

6-tert-Butyl-2-[3-(5-{5-[2-(3,3-difluoro-azetidin-1-yl)-1,1-dimethyl-ethoxy]-pyridin-2-ylamino}-1-methyl-6-oxo-1,6-dihydro-pyridazin-3-yl)-2-hydroxymethyl-phenyl]-2H-phthalazin-1-one; and 2-(2-{2-Hydroxymethyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-1-oxo-1,2,3,4-tetrahydro-isoquinolin-6-yl)-2-methyl-propionitrile.

The application provides a method for treating an inflammatory or autoimmune condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a pharmaceutical composition comprising the compound of Formula I.

The application provides a pharmaceutical composition comprising the compound of Formula I, admixed with at least one pharmaceutically acceptable carrier, excipient or diluent.

The application provides a use of the compound of formula I in the manufacture of a medicament for the treatment of an inflammatory disorder.

The application provides a use of the compound of formula I in the manufacture of a medicament for the treatment of an autoimmune disorder.

The application provides a use of the compound of formula I in the manufacture of a medicament for the treatment of rheumatoid arthritis.

The application provides a use of the compound of formula I in the manufacture of a medicament for the treatment of asthma.

The application provides the use of a compound as described above for the treatment of inflammatory or autoimmune disorder.

The application provides the use of a compound as described above for the treatment of rheumatoid arthritis.

The application provides the use of a compound as described above for the treatment of asthma.

The application provides a compound as described above for use in the treatment of inflammatory or autoimmune condition disorder.

The application provides a compound as described above for use in the treatment of rheumatoid arthritis.

The application provides a compound as described above for use in the treatment of asthma.

The application provides a compound, method, or composition as described herein.

The application provides a method for treating an inflammatory or autoimmune disorder comprising administering to a patient in need thereof a therapeutically effective amount of the Btk inhibitor compound of Formula I'.

The application provides a method for treating arthritis comprising administering to a patient in need thereof a therapeutically effective amount of the Btk inhibitor compound of Formula I'.

The application provides a method for treating asthma comprising administering to a patient in need thereof a therapeutically effective amount of the Btk inhibitor compound of Formula I'.

The application provides a method of inhibiting B-cell proliferation comprising administering to a patient in need thereof a therapeutically effective amount of the Btk inhibitor compound of Formula I'.

The application provides a method for inhibiting Btk activity comprising administering the Btk inhibitor compound of any one of Formula I', wherein the Btk inhibitor compound exhibits an $IC_{50}$ of 50 micromolar or less in an in vitro biochemical assay of Btk activity.

In one variation of the above method, the Btk inhibitor compound exhibits an $IC_{50}$ of 100 nanomolar or less in an in vitro biochemical assay of Btk activity.

In another variation of the above method, the compound exhibits an $IC_{50}$ of 10 nanomolar or less in an in vitro biochemical assay of Btk activity.

The application provides a method for treating an inflammatory condition comprising co-administering to a patient in need thereof a therapeutically effective amount of an anti-inflammatory compound in combination with the Btk inhibitor compound of Formula I.

The application provides a method for treating arthritis comprising co-administering to a patient in need thereof a therapeutically effective amount of an anti-inflammatory compound in combination with the Btk inhibitor compound of Formula I.

The application provides a method for treating a lymphoma or a BCR-ABL1[+] leukemia cells by administering to a patient in need thereof a therapeutically effective amount of the Btk inhibitor compound of Formula I.

The application provides a pharmaceutical composition comprising the Btk inhibitor compound of Formula', admixed with at least one pharmaceutically acceptable carrier, excipient or diluent.

The application provides a use of the compound of formula I in the manufacture of a medicament for the treatment of an inflammatory disorder.

The application provides a use of the compound of formula I' in the manufacture of a medicament for the treatment of an autoimmune disorder.

The application provides a compound, method, or composition as described herein.

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of pyridazinone compounds according to generic Formula I:

TABLE I

| Compound | Nomenclature | Structure |
| --- | --- | --- |
| I-1 | 2-(3-{5-[5-(2-Azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-6-tert-butyl-2H-phthalazin-1-one | 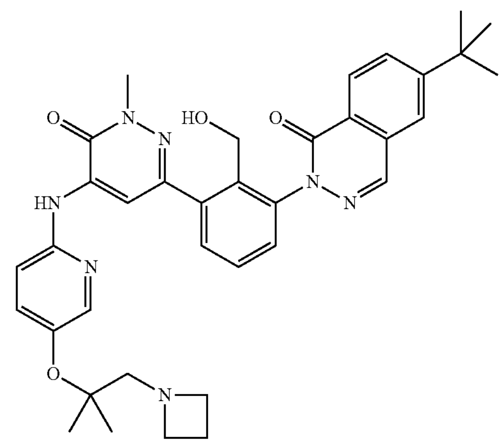 [SMILES: Cn1nc(-c2cccc(-n3ncc4cc(C(C)(C)C)ccc4c3=O)c2CO)cc(Nc2ccc(OC(C)(C)CN3CCC3)cn2)c1=O] |
| I-2 | 6-tert-Butyl-2-{2-hydroxymethyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-2H-phthalazin-1-one | 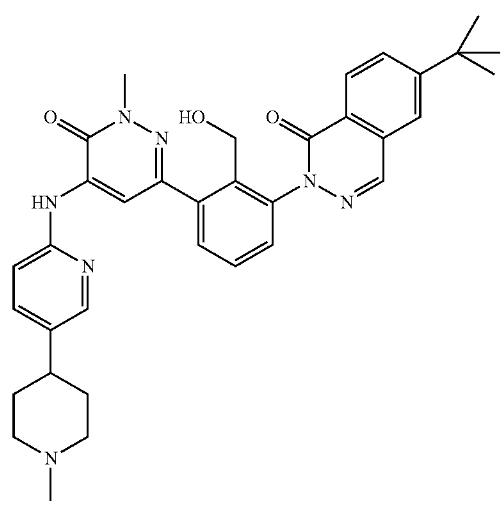 [SMILES: CN1CCC(c2ccc(Nc3cc(-c4cccc(-n5ncc6cc(C(C)(C)C)ccc6c5=O)c4CO)nn(C)c3=O)nc2)CC1] |

TABLE I-continued

| Compound | Nomenclature | Structure |
|---|---|---|
| I-3 | 2-{3-[5-(5-Azetidin-1-ylmethyl-1-methyl-1H-pyrazol-3-ylamino)-1-methyl-6-oxo-1,6-dihydro-pyridazin-3-yl]-2-hydroxymethyl-phenyl}-6-tert-butyl-2H-phthalazin-1-one | 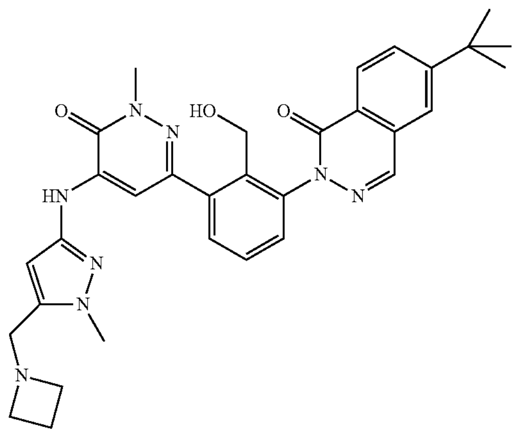 [SMILES: Cn1nc(Nc2cc(-c3cccc(-n4ncc5cc(C(C)(C)C)ccc5c4=O)c3CO)nn(C)c2=O)cc1CN1CCC1] |
| I-4 | 6-tert-Butyl-2-(2-hydroxymethyl-3-{1-methyl-5-[5-((S)-1-methyl-pyrrolidin-2-yl)-pyridin-2-ylamino]-6-oxo-1,6-dihydro-pyridazin-3-yl}-phenyl)-2H-phthalazin-1-one | 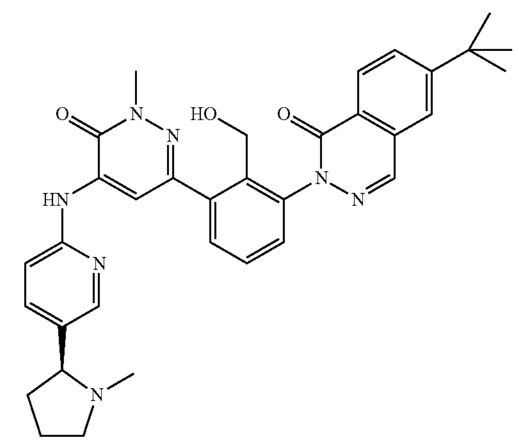 [SMILES: CN1CCC[C@H]1c1ccc(Nc2cc(-c3cccc(-n4ncc5cc(C(C)(C)C)ccc5c4=O)c3CO)nn(C)c2=O)nc1] |
| I-5 | 6-tert-Butyl-2-(2-hydroxymethyl-3-{1-methyl-5-[5-((S)-1-methyl-pyrrolidin-3-yl)-pyridin-2-ylamino]-6-oxo-1,6-dihydro-pyridazin-3-yl}-phenyl)-2H-phthalazin-1-one | 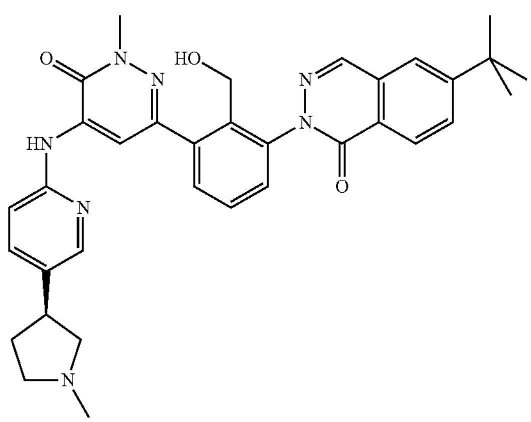 [SMILES: CN1CC[C@@H](c2ccc(Nc3cc(-c4cccc(-n5ncc6cc(C(C)(C)C)ccc6c5=O)c4CO)nn(C)c3=O)nc2)C1] |

TABLE I-continued

| Compound | Nomenclature | Structure |
|---|---|---|
| I-6 | 6-tert-Butyl-2-(2-hydroxymethyl-3-{1-methyl-5-[5-((R)-1-methyl-pyrrolidin-3-yl)-pyridin-2-ylamino]-6-oxo-1,6-dihydro-pyridazin-3-yl}-phenyl)-2H-phthalazin-1-one | 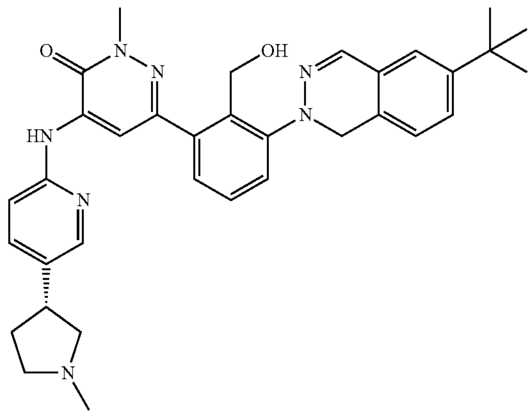 [SMILES: CN1CC[C@H](c2ccc(Nc3cc(-c4cccc(N5Cc6ccc(C(C)(C)C)cc6C=N5)c4CO)nn(C)c3=O)nc2)C1] |
| I-7 | 2-(2-{2-Hydroxymethyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-1-oxo-1,2-dihydro-phthalazin-6-yl)-2-methyl-propionitrile | 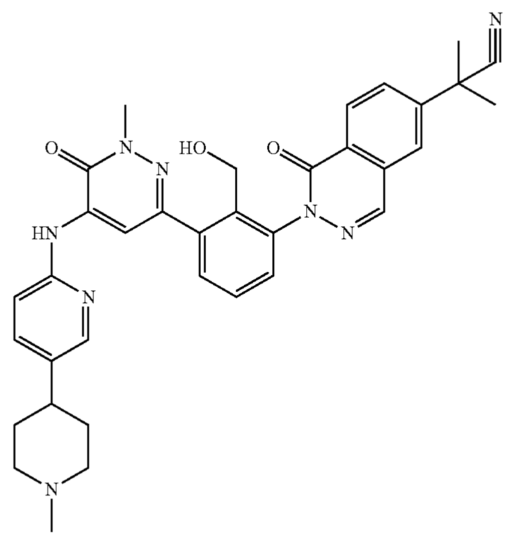 [SMILES: CN1CCC(c2ccc(Nc3cc(-c4cccc(-n5ncc6cc(C(C)(C)C#N)ccc6c5=O)c4CO)nn(C)c3=O)nc2)CC1] |
| I-8 | 6-tert-Butyl-2-{2-hydroxymethyl-3-[1-methyl-5-(5-methyl-4,5,6,7-tetrahydro-pyrazolo[1,5-a]pyrazin-2-ylamino)-6-oxo-1,6-dihydro-pyridazin-3-yl]-phenyl}-2H-phthalazin-1-one | 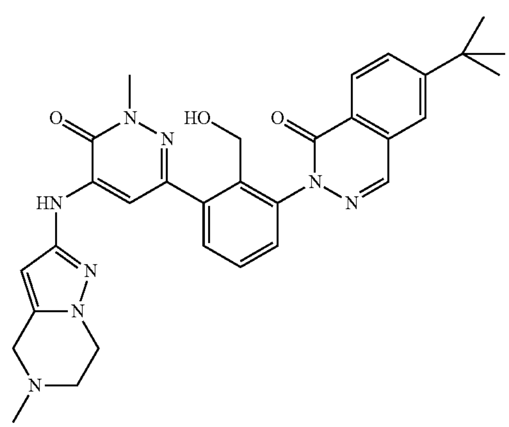 [SMILES: CN1CCn2nc(Nc3cc(-c4cccc(-n5ncc6cc(C(C)(C)C)ccc6c5=O)c4CO)nn(C)c3=O)cc2C1] |

TABLE I-continued

| Compound | Nomenclature | Structure |
|---|---|---|
| I-9 | 6-tert-Butyl-2-{3-[5-(1'-ethyl-1',2',3',4',5',6'-hexahydro-[3,4']bipyridinyl-6-ylamino)-1-methyl-6-oxo-1,6-dihydro-pyridazin-3-yl]-2-hydroxymethyl-phenyl}-2H-phthalazin-1-one | 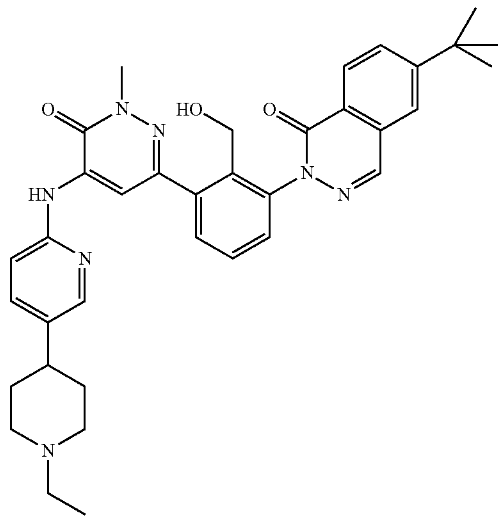 [SMILES: CCN1CCC(c2ccc(Nc3cc(-c4cccc(-n5ncc6cc(C(C)(C)C)ccc6c5=O)c4CO)nn(C)c3=O)nc2)CC1] |
| I-10 | 6-tert-Butyl-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-2H-phthalazin-1-one | 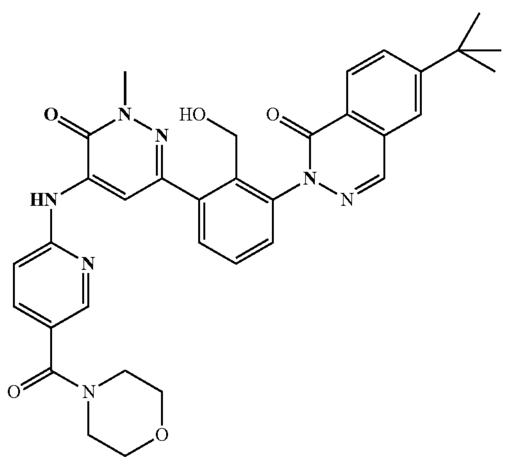 [SMILES: Cn1nc(-c2cccc(-n3ncc4cc(C(C)(C)C)ccc4c3=O)c2CO)cc(Nc2ccc(C(=O)N3CCOCC3)cn2)c1=O] |
| I-11 | 2-[2-(3-{5-[5-(2-Azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-1-oxo-1,2-dihydro-phthalazin-6-yl]-2-methyl-propionitrile | 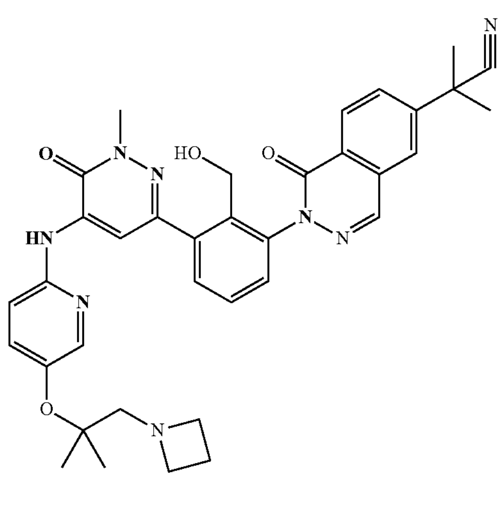 [SMILES: Cn1nc(-c2cccc(-n3ncc4cc(C(C)(C)C#N)ccc4c3=O)c2CO)cc(Nc2ccc(OC(C)(C)CN3CCC3)cn2)c1=O] |

TABLE I-continued

| Compound | Nomenclature | Structure |
|---|---|---|
| I-12 | 6-tert-Butyl-2-[2-hydroxymethyl-3-(5-{5-[2-(3-hydroxy-propylamino)-1,1-dimethyl-ethoxy]-pyridin-2-ylamino}-1-methyl-6-oxo-1,6-dihydro-pyridazin-3-yl)-phenyl]-2H-phthalazin-1-one | 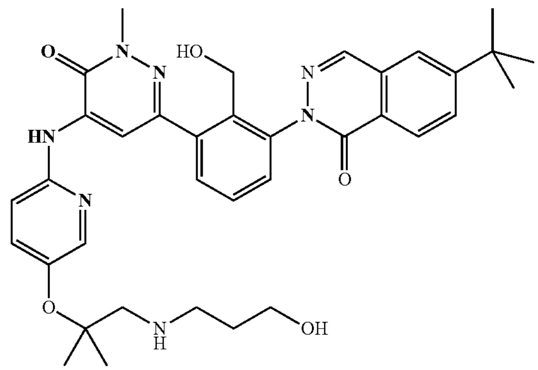 [SMILES: Cn1nc(-c2cccc(-n3ncc4cc(C(C)(C)C)ccc4c3=O)c2CO)cc(Nc2ccc(OC(C)(C)CNCCCO)cn2)c1=O] |
| I-13 | 6-tert-Butyl-2-{2-hydroxymethyl-3-[1-methyl-5-(1'-oxetan-3-yl-1',2',3',4',5',6'-hexahydro-[3,4']bipyridinyl-6-ylamino)-6-oxo-1,6-dihydro-pyridazin-3-yl]-phenyl}-2H-phthalazin-1-one | 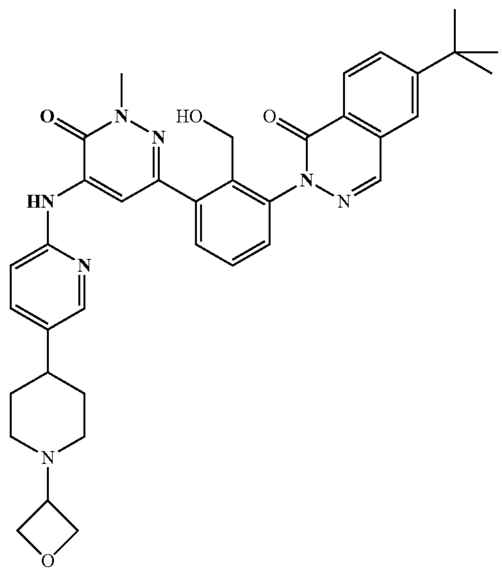 [SMILES: Cn1nc(-c2cccc(-n3ncc4cc(C(C)(C)C)ccc4c3=O)c2CO)cc(Nc2ccc(C3CCN(C4COC4)CC3)cn2)c1=O] |
| I-14 | 6-tert-Butyl-2-[3-(5-{5-[2-(3,3-difluoro-azetidin-1-yl)-1,1-dimethyl-ethoxy]-pyridin-2-ylamino}-1-methyl-6-oxo-1,6-dihydro-pyridazin-3-yl)-2-hydroxymethyl-phenyl]-2H-phthalazin-1-one | 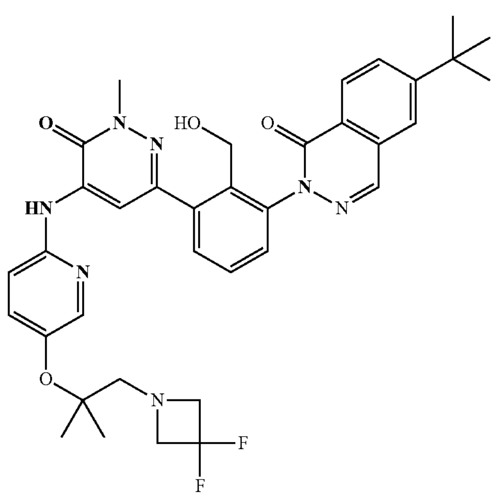 [SMILES: Cn1nc(-c2cccc(-n3ncc4cc(C(C)(C)C)ccc4c3=O)c2CO)cc(Nc2ccc(OC(C)(C)CN3CC(F)(F)C3)cn2)c1=O] |

TABLE I-continued

| Compound | Nomenclature | Structure |
|---|---|---|
| I-15 | 2-(2-{2-Hydroxymethyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-1-oxo-1,2,3,4-tetrahydro-isoquinolin-6-yl)-2-methyl-propionitrile | 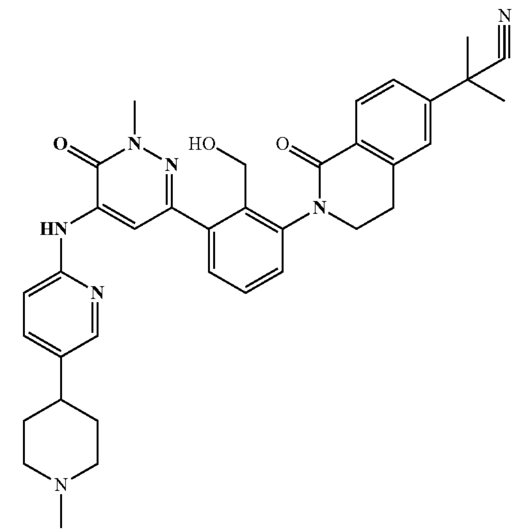 [SMILES: CN1CCC(c2ccc(Nc3cc(-c4cccc(N5CCc6cc(C(C)(C)C#N)ccc6C5=O)c4CO)nn(C)c3=O)nc2)CC1] |

General Synthetic Schemes

The application provides a process of preparing the compound of Formula II, wherein $Y_1$ is boronic acid or pinacol boronate, comprising the step of:

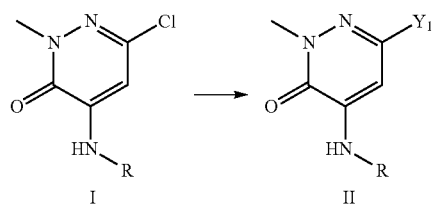

heating a compound of formula I to about 40° C. to 150° C., in the presence of bis(pinacolato)diboron, a palladium catalyst, a base, and a phosphine.

The application provides the above process, wherein the phosphine is PCy3, an alkyl mono-phosphine compound, an aryl mono-phosphine compound, an alkyl diphosphine compounds or an aryl di-phosphine compound.

The application provides the above process, wherein the base is an inorganic base including potassium carbonate, cesium carbonate, potassium phosphate and potassium acetate, or an amine base, including dicyclohexylamine and triethylamine.

The application provides the above process, wherein the palladium catalyst is palladium(II) acetate or bis(dibenzylideneacetone)palladium(0), tris(dibenzylideneacetone)dipalladium(0), or the like.

The application provides a process of preparing the compound of Formula IV, comprising the steps of:

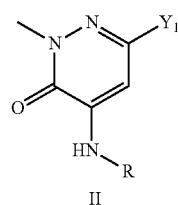

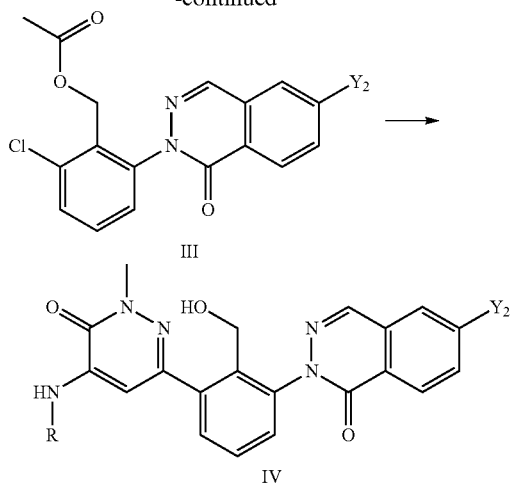

a) heating a compound of Formula II, wherein $Y_1$ is boronic acid or pinacol boronate or a mixture of the two, to about 40° C. to 150° C., in the presence of a compound of formula III, a palladium catalyst, base, and a phosphine; and b) treating the product of step a) with a base such as sodium hydroxide or potassium hydroxide or potassium carbonate or cesium carbonate in a solvent such as methanol at a temperature between about room temperature and about 40° C.

The application provides the above process, wherein the phosphine is PCy3, an alkyl mono-phosphine compound, an aryl mono-phosphine compound, an alkyl diphosphine compounds or an aryl di-phosphine compound.

The application provides the above process, wherein the base is an inorganic base including potassium carbonate, cesium carbonate, potassium phosphate and potassium acetate, or an amine base, including dicyclohexylamine and triethylamine.

The application provides the above process, wherein the palladium catalyst is palladium(II) acetate or bis(dibenzylideneacetone)palladium(0), tris(dibenzylideneacetone)dipalladium(0), or the like.

The application provides a process of preparing the compound of Formula IV, comprising the steps of:

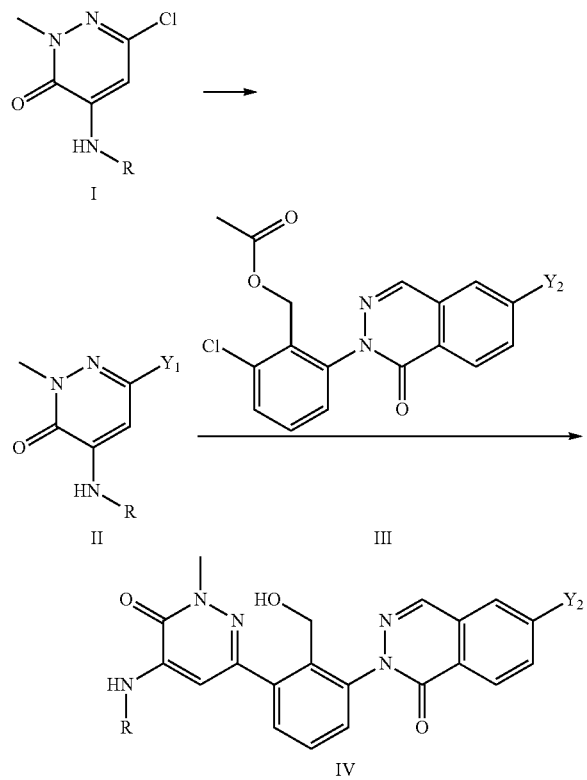

a) heating a compound of formula I to about 40° C. to 150° C., in the presence of bis(pinacolato)diboron, a palladium catalyst, a base, and a phosphine;

b) heating the product of step a) without isolation with a compound of Formula III to about 40° C. to 150° C., in the presence of a compound of formula VII, a palladium catalyst, base, and a phosphine; and c) treating the product of step b) with a base such as sodium hydroxide or potassium hydroxide or potassium carbonate or cesium carbonate in a solvent such as methanol at a temperature between about room temperature and about 40° C.

The application provides a process of preparing the compound of Formula IV, comprising the steps of:

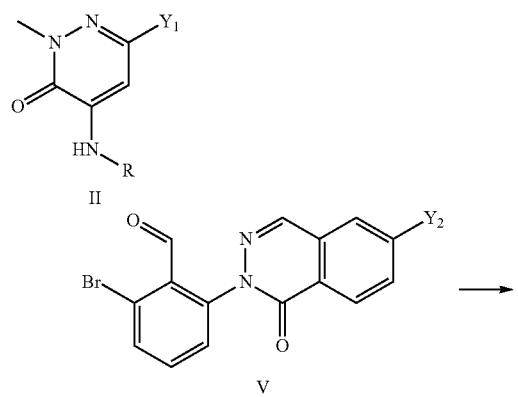

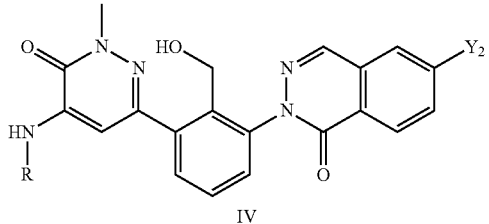

a) heating a compound of Formula II, wherein $Y_1$ is boronic acid or pinacol boronate or a mixture of the two, to about 40° C. to 150° C., in the presence of a compound of formula V, a palladium catalyst, base, and a phosphine; and b) treating the product of step a) with a reducing agent such as sodium borohydride or the like in a solvent such as methanol or a mixture of methanol and water at a temperature around room temperature.

The application provides the above process, wherein the phosphine is PCy3, an alkyl mono-phosphine compound, an aryl mono-phosphine compound, an alkyl diphosphine compounds or an aryl di-phosphine compound.

The application provides the above process, wherein the base is an inorganic base including potassium carbonate, cesium carbonate, potassium phosphate and potassium acetate, or an amine base, including dicyclohexylamine and triethylamine.

The application provides the above process, wherein the palladium catalyst is palladium(II) acetate or bis(dibenzylideneacetone)palladium(0), tris(dibenzylideneacetone) dipalladium(0), or the like.

The application provides a process of preparing the compound of Formula VII, comprising the steps of:

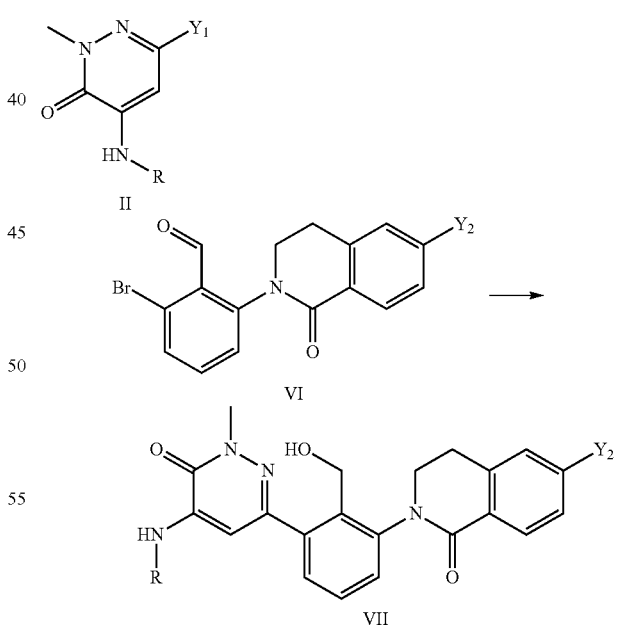

a) heating a compound of Formula II, wherein $Y_1$ is boronic acid or pinacol boronate or a mixture of the two, to about 40° C. to 150° C., in the presence of a compound of formula VI, a palladium catalyst, base, and a phosphine; and b) treating the product of step a) with a reducing agent such as sodium borohydride or the like in a solvent such as methanol or a mixture of methanol and water at a temperature around room temperature.

The application provides the above process, wherein the phosphine is PCy3, an alkyl mono-phosphine compound, an aryl mono-phosphine compound, an alkyl diphosphine compounds or an aryl di-phosphine compound.

The application provides the above process, wherein the base is an inorganic base including potassium carbonate, cesium carbonate, potassium phosphate and potassium acetate, or an amine base, including dicyclohexylamine and triethylamine.

The application provides the above process, wherein the palladium catalyst is palladium(II) acetate or bis(dibenzylideneacetone)palladium(0), tris(dibenzylideneacetone) dipalladium(0), or the like.

The application provides a process of preparing the compound of Formula VIII, wherein $Y_1$ is boronic acid or pinacol boronate, comprising the step of:

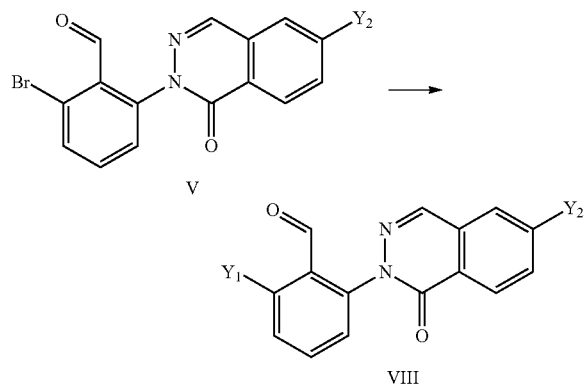

heating a compound of formula V in the presence of bis(pinacolato)diboron, a palladium catalyst, a base, and a phosphine The application provides the above process, wherein the phosphine is PCy3, an alkyl mono-phosphine compound, an aryl mono-phosphine compound, an alkyl diphosphine compounds or an aryl di-phosphine compound.

The application provides the above process, wherein the base is an inorganic base including potassium carbonate, cesium carbonate, potassium phosphate and potassium acetate, or an amine base, including dicyclohexylamine and triethylamine.

The application provides the above process, wherein the palladium catalyst is palladium(II) acetate or bis(dibenzylideneacetone)palladium(0), tris(dibenzylideneacetone) dipalladium(0), or the like.

The application provides a process of preparing the compound of Formula IV, comprising the steps of:

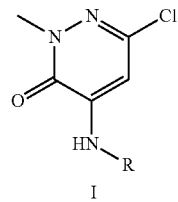

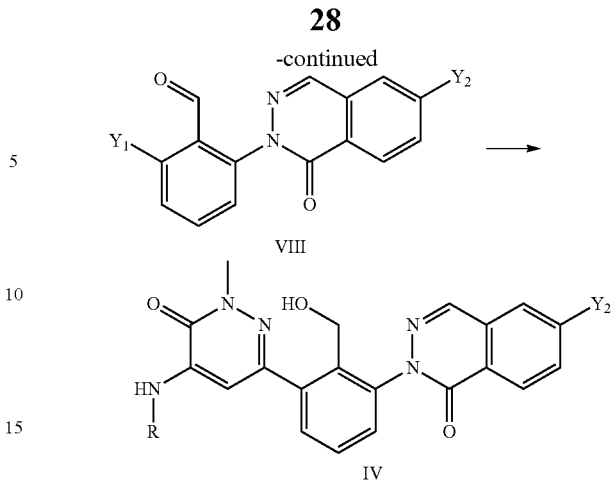

a) heating a compound of Formula VIII, wherein $Y_1$ is boronic acid or pinacol boronate or a mixture of the two, to about 40° C. to 150° C., in the presence of a compound of formula I, a palladium catalyst, base, and a phosphine; and b) treating the product of step a) with a reducing agent such as sodium borohydride or the like in a solvent such as methanol or a mixture of methanol and water at a temperature around room temperature.

The application provides the above process, wherein the phosphine is PCy3, an alkyl mono-phosphine compound, an aryl mono-phosphine compound, an alkyl diphosphine compounds or an aryl di-phosphine compound.

The application provides the above process, wherein the base is an inorganic base including potassium carbonate, cesium carbonate, potassium phosphate and potassium acetate, or an amine base, including dicyclohexylamine and triethylamine.

The application provides the above process, wherein the palladium catalyst is palladium(II) acetate or bis(dibenzylideneacetone)palladium(0), tris(dibenzylideneacetone) dipalladium(0), or the like.

Pharmaceutical Compositions and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid. Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Indications and Methods of Treatment

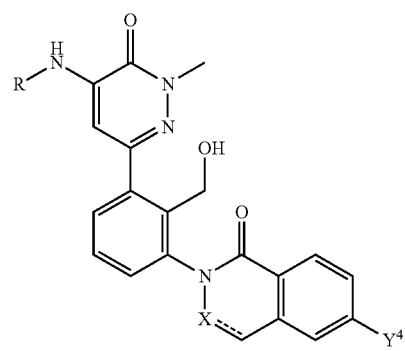

I

The compounds of generic Formula I inhibit Bruton's tyrosine kinase (Btk). Activation of Btk by upstream kinases results in activation of phospholipase-Cγ which, in turn, stimulates release of pro-inflammatory mediators. The compounds of generic Formula I, incorporating 1-oxo-1H-phthalazin-2-yl side chains exhibit unexpectedly enhanced inhibitory activity compared to analogues with other side chains. The hydroxymethyl substitution on the phenyl ring further provides unexpectedly increased potency and compared to analogues with alternative substitution at that position. Compounds of Formula I are useful in the treatment of arthritis and other anti-inflammatory and autoimmune diseases. Compounds according to Formula I are, accordingly, useful for the treatment of arthritis. Compounds of Formula I are useful for inhibiting Btk in cells and for modulating B-cell development. The present invention further comprises pharmaceutical compositions containing compounds of Formula I admixed with pharmaceutically acceptable carrier, excipients or diluents.

The compounds described herein are kinase inhibitors, in particular Btk inhibitors. These inhibitors can be useful for treating one or more diseases responsive to kinase inhibition, including diseases responsive to Btk inhibition and/or inhibition of B-cell proliferation, in mammals. Without wishing to be bound to any particular theory, it is believed that the interaction of the compounds of the invention with Btk results in the inhibition of Btk activity and thus in the pharmaceutical utility of these compounds. Accordingly, the invention includes a method of treating a mammal, for instance a human, having a disease responsive to inhibition of Btk activity, and/or inhibiting B-cell proliferation, comprising administrating to the mammal having such a disease, an effective amount of at least one chemical entity provided herein. An effective concentration may be ascertained experimentally, for example by assaying blood concentration of the compound, or theoretically, by calculating bioavailability. Other kinases that may be affected in addition to Btk include, but are not limited to, other tyrosine kinases and serine/threonine kinases.

Kinases play notable roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

An embodiment includes a method of treating a patient having an autoimmune and/or inflammatory disease, or an acute inflammatory reaction responsive to inhibition of Btk activity and/or B-cell proliferation.

Autoimmune and/or inflammatory diseases that can be affected using compounds and compositions according to the invention include, but are not limited to: psoriasis, allergy, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic Idiopathic thrombocytopenic purpura (ITP), Addison's disease, Parkinson's disease, Alzheimer's disease, diabetes, septic shock, and myasthenia gravis.

Included herein are methods of treatment in which at least one chemical entity provided herein is administered in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

B-cells and B-cell precursors expressing Btk have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., *J. Biol. Chem.* 1998, 274, 1646-1656).

It has also been discovered that BTK inhibitors are useful as chemosensitizing agents, and, thus, are useful in combination with other chemotherapeutic drugs, in particular, drugs that induce apoptosis. Examples of other chemotherapeutic drugs that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Btk activity has also been associated with some leukemias expressing the bcr-abl fusion gene resulting from translocation of parts of chromosome 9 and 22. This abnormality is commonly observed in chronic myelogenous leukemia. Btk is constitutively phosphorylated by the bcr-abl kinase which initiates downstream survival signals which circumvents apoptosis in bcr-abl cells. (N. Feldhahn et al. *J. Exp. Med.* 2005 201(11):1837-1852).

Methods of Treatment

The application provides a method for treating an inflammatory and/or autoimmune condition comprising administering to a patient in need thereof a therapeutically effective amount of the compound of Formula I.

The application provides a method for treating an inflammatory condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of Formula I.

The application provides a method for treating an inflammatory and/or autoimmune condition comprising administering to a patient in need thereof a therapeutically effective amount of the Btk inhibitor compound of Formulae I.

The application provides a method for treating arthritis comprising administering to a patient in need thereof a therapeutically effective amount of the Btk inhibitor compound of Formula I.

The application provides a method for treating asthma comprising administering to a patient in need thereof a therapeutically effective amount of the Btk inhibitor compound of Formula I.

The application provides a method of inhibiting B-cell proliferation comprising administering to a patient in need thereof a therapeutically effective amount of the Btk inhibitor compound of Formula I.

The application provides a method for inhibiting Btk activity comprising administering the Btk inhibitor compound of any one of Formula I, wherein the Btk inhibitor compound exhibits an $IC_{50}$ of 50 micromolar or less in an in vitro biochemical assay of Btk activity.

In one variation of the above method, the Btk inhibitor compound exhibits an $IC_{50}$ of 100 nanomolar or less in an in vitro biochemical assay of Btk activity.

In another variation of the above method, the compound exhibits an $IC_{50}$ of 10 nanomolar or less in an in vitro biochemical assay of Btk activity.

The application provides a method for treating an inflammatory condition comprising co-administering to a patient in need thereof a therapeutically effective amount of an anti-inflammatory compound in combination with the Btk inhibitor compound of Formula I.

The application provides a method for treating arthritis comprising co-administering to a patient in need thereof a therapeutically effective amount of an anti-inflammatory compound in combination with the Btk inhibitor compound of Formula I.

The application provides a method for treating a lymphoma or a BCR-ABL1+ leukemia cells by administering to a patient in need thereof a therapeutically effective amount of the Btk inhibitor compound of Formula I.

EXAMPLES

Abbreviations

Commonly used abbreviations include: acetyl (Ac), azobis-isobutyrylnitrile (AIBN), atmospheres (Atm), 9-borabicyclo[3.3.1]nonane (9-BBN or BBN), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano-1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether ($Et_2O$), ethyl isopropyl ether (EtOiPr), O-(7-azabenzotriazol-1-yl)-N, N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), isopropylmagnesium chloride (iPrMgCl), hexamethyl disilazane (HMDS), liquid chromatography mass spectrometry (LCMS), lithium hexamethyl disilazane (LiHMDS), meta-chloroperoxybenzoic acid (m-CPBA), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpholine (NMM), N-methylpyrrolidone (NMP), pyridinium chlorochromate (PCC), Dichloro-((bis-diphenylphosphino)ferrocenyl) palladium(II) ($Pd(dppf)Cl_2$), palladium(II) acetate ($Pd(OAc)_2$), tris(dibenzylideneacetone)dipalladium(0) ($Pd_2(dba)_3$), pyridinium dichromate (PDC), phenyl (Ph), propyl (Pr), iso-propyl (i-Pr), pounds per square inch (psi), pyridine (pyr), 1,2,3,4,5-Pentaphenyl-1'-(di-tert-butylphosphino)ferrocene (Q-Phos), room temperature (ambient temperature, rt or RT), sec-Butyllithium (sBuLi), tert-butyldimethylsilyl or t-$BuMe_2Si$ (TBDMS), tetra-n-butylammonium fluoride (TBAF), triethylamine (TEA or $Et_3N$), 2,2,6,6-tetramethylpiperidine 1-oxyl (TEMPO), trimethylsilylethoxymethyl (SEM), triflate or $CF_3SO_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or $Me_3Si$ (TMS), p-toluenesulfonic acid monohydrate (TsOH or pTsOH), 4-Me-C$_6$H$_4$SO$_2$— or tosyl (Ts), and N-urethane-N-carboxy-anhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford).

General Conditions

Compounds of the present invention can be prepared beginning with the commercially available starting materials by utilizing general synthetic techniques and procedures known to those skilled in the art. Outlines below are reaction schemes suitable for preparing such compounds. Further exemplification can be found in the specific examples.

Preparative Examples

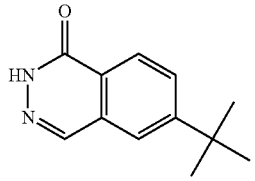

6-tert-Butyl-2H-phthalazin-1-one

In a 1 L round-bottomed flask, 4-tert-butylbenzoyl chloride (97.2 g, 90 ml, 494 mmol, Eq: 1.00) was combined with CH$_2$Cl$_2$ (375 ml) to give a colorless solution. Cooled to 0° C. 2-methylpropan-2-amine (79.5 g, 114 ml, 1.09 mol, Eq: 2.2) was added dropwise from a dropping funnel, maintaining the temperature below 10° C. The sides of the addition funnel were rinsed down with more CH$_2$Cl$_2$. The reaction was allowed to warm to 25° C. over 3 h. 4N NaOH was added slowly until the solids mostly dissolved (approx. 300 mL). The layers were separated. The aqueous layer was extracted 4× CH$_2$Cl$_2$. The organic layers (2.5 L total) were dried over Na$_2$SO$_4$ and concentrated to about 250 mL. A lot of precipitate had formed. The flask was cooled in ice bath. The resulting white solid was filtered and washed 3× CH$_2$Cl$_2$ and 1× EtOAc. to afford a white solid as needles (72 g) which was dried under vacuum on the pump. The combined filtrate and washes were conc. again to 100 mL. More crystals formed. Cooled. Filtered and washed with CH$_2$Cl$_2$ to afford a second crop of a white solid. (31.6 g). $^1$H NMR (300 MHz, CHLOROFORM-d) δ ppm 1.33 (s, 9H) 1.47 (s, 9H) 5.91 (br. s., 1H) 7.43 (d, J=8.31 Hz, 2H) 7.66 (d, J=8.31 Hz, 2H)

This reaction was run in 2×26 g batches and combined for workup. For each batch, a 2 L three-necked flask fitted with a mechanical stirrer, an addition funnel with line to a bubbler, and a nitrogen inlet. The system was heated in the drying oven and cooled under a stream of N$_2$. N,4-di-tert-butylbenzamide (26.2 g, 112 mmol, Eq: 1.00) was combined with THF (1.01 l) to give a colorless solution. The reaction mixture was cooled to −78° C. The sec-butyllithium in cyclohexanes (176 ml of 1.4 M, 247 mmol, Eq: 2.2) was added dropwise slowly and with a stream of N$_2$. A yellow solution resulted. The reaction mixture was warmed to −15° C. over 1 h.

A yellow suspension resulted. The reaction mixture was cooled back to −78° C. Dry DMF (16.4 g, 17.4 ml, 225 mmol, Eq: 2) was added dropwise. The reaction was allowed to warm to 0° C. LCMS indicated reaction had gone to completion.

150 mL of sat'd NH$_4$Cl was added slowly at 0° C. The reaction mixture was allowed to sit at ambient temperature and then was transferred to a 4 L erlenmeyer and washed down with water and EtOAc. The two batches were combined and then transferred to the same 4 L erlenmeyer.

The total volume of the 2 reaction mixtures was a little over 3 L. The reaction mixture was concentrated down carefully on the rotoevaporator at 50° C. in portions in a 2 L roundbottom flask to avoid bumping. The volume was reduced to approximately 200-300 mL.

There was lots of solid precipitate. LCMS indicated no product in the liquid portion. The white solid was collected by filtration in a large sintered glass funnel. The chunks were suspended in water in the funnel and broken up to a fine powder with a pestle and filtered. The solid was washed 5 times with water and then dried in a vacuum oven at 50° C. for 2 days to afford 59.6 g of 2,5-di-tert-butyl-3-hydroxy-isoindolin-1-one of an off-white solid. $^1$H nmr and was carried on to the next step as is. $^1$H NMR (300 MHz, CHLOROFORM-d) δ ppm 7.27 (s, 9H) 7.53 (s, 9H) 8.26 (d, J=11.71 Hz, 1H) 11.90 (d, J=11.71 Hz, 1H) 13.40-13.46 (m, 1H) 13.47 (s, 1H) 13.51-13.58 (m, 1H).

In a 2 L three-necked flask equipped with an addition funnel, air-cooled condenser, and nitrogen inlet 2,5-di-tert-butyl-3-hydroxyisoindolin-1-one (59.6 g, 228 mmol, Eq: 1.00) was combined with acetic acid (868 ml) to give a light yellow solution. The reaction was heated to 90° C. Hydrazine monohydrate (14.8 g, 14.4 ml, 296 mmol, Eq: 1.3) was added dropwise. The reaction mixture was stirred at 90° C. for 1 h before the reaction mixture was diluted with 300 mL H$_2$O and slowly allowed to cool to 25° C. LCMS showed that the reaction was complete with clean conversion to the desired product. The reaction was concentrated to a reduced volume (approx. 50-100 mL). A colorless solid came out of solution on standing. The solid was collected by filtration, washed several times with water, 1× ether and 2× ether/hexanes and dried under vacuum to afford 6-tert-Butyl-2H-phthalazinone (37 g, 82% yield) as a white solid. $^1$H NMR (400 MHz, CHLOROFORM-d) δ ppm 1.44 (s, 9H) 7.66-7.73 (m, 1H) 7.84-7.91 (m, 1H) 8.18 (d, J=0.51 Hz, 1H) 8.33-8.42 (m, 1H).

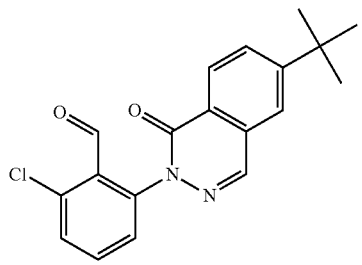 [SMILES: CC(C)(C)c1ccc2c(=O)n(-c3cccc(Cl)c3C=O)ncc2c1]

2-(6-tert-Butyl-1-oxo-1H-phthalazin-2-yl)-6-chlorobenzaldehyde

In a 500 mL three-necked flask fitted with a N$_2$ inlet and a bubbler outlet and a mechanical stirrer, 6-tert-butyl-phthalazin-1(2H)-one (6.46 g, 31.9 mmol, Eq: 1.00), 2-chloro-6-fluorobenzaldehyde (7.6 g, 47.9 mmol, Eq: 1.5) and potassium carbonate (8.83 g, 63.9 mmol, Eq: 2)(fine powder) were combined with DMA (70 ml) to give a yellow suspension. Tetraethylammonium chloride (688 mg, 4.15 mmol, Eq: 0.13) was added and the reaction mixture was warmed at 68° C. (bath temp) with vigorous stirring. After the reaction mixture became a solution it was stirred at this temperature for 1 h. The reaction was continued to be warmed at 75° C. (bath temperature) overnight. Additional 2-chloro-6-fluorobenzaldehyde (5 g, 31.9 mmol, Eq: 1.00) was added and the reaction mixture was warmed at 75° C. (bath temperature) 3 days. The reaction mixture was poured into 300 mL $H_2O$ and extracted with $CH_2Cl_2$ (5×300 mL). The organic layers were dried over $Na_2SO_4$ and concentrated in vacuo. A large volume of DMA remained. The reaction mixture was poured into 500 mL $H_2O$ and extracted with diethyl ether (5×300 mL). The ethereal layer was washed with brine, dried over $MgSO_4$, filtered and concentrated in vacuo. When the volume was approximately 150 mL there was a lot of white crystalline material. Product was isolated by filtration to afford pure product (5.4 g). The filtrate was concentrated in vacuo and the residue was purified using an Analogix purification system with an SF25-160 g column (eluting with 5-25% (3:1 $CH_2Cl_2$/EtOAc)/hexane to afford an additional 4.75 g the desired product. Total yield of 2-(6-tert-Butyl-1-oxo-1H-phthalazin-2-yl)-6-chloro-benzaldehyde was 10.1 g (93%). $^1H$ NMR (300 MHz, CHLOROFORM-d) δ ppm 7.27 (s, 9H) 13.30 (d, J=7.55 Hz, 1H) 13.34-13.51 (m, 2H) 13.56 (d, J=1.51 Hz, 1H) 13.71 (dd, J=8.50, 1.70 Hz, 1H) 14.12 (s, 1H) 14.21 (d, J=8.31 Hz, 1H) 16.20 (s, 1H). LC/MS observed [M+H]$^+$ 340.8; [M+Na]$^+$ 362.9.

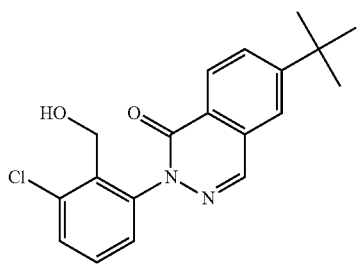 [SMILES: CC(C)(C)c1ccc2c(=O)n(-c3cccc(Cl)c3CO)ncc2c1]

6-tert-Butyl-2-(3-chloro-2-hydroxymethyl-phenyl)-2H-phthalazin-1-one

To a solution of 2-(6-tert-butyl-1-oxophthalazin-2(1H)-yl)-6-chlorobenzaldehyde (61 g, 179 mmol, Eq: 1.00) in $CH_2Cl_2$ (350 ml) and methanol (350 ml) was added sodium borohydride (7.45 g, 197 mmol, Eq: 1.1) in 1 g portions over 20 min with vigorous stirring at 0° C. and under a stream of nitrogen. The reaction mixture was allowed to warm to ambient temperature and was stirred at this temperature for 1 h. Water (100 mL) was added dropwise followed by $CH_2Cl_2$ and more water and the layers were separated. The aqueous phase was extracted 3× with $CH_2Cl_2$. The combined organic layers were washed with saturated $NH_4Cl$ and dried over sodium sulfate. After filtration the yellow liquid was concentrated to afford a yellow-green solid. This solid was triturated with ether/ethyl acetate 6:1 and washed several times with the same solvent to afford a pale yellow-green solid. This solid was slurried in dichloromethane with 1% methanol. The resulting white solid was collected by filtration, washed with dichloromethane and then with dichloromethane/ether to afford the 6-tert-Butyl-2-(3-chloro-2-hydroxymethyl-phenyl)-2H-phthalazin-1-one as a white solid. (28.3 g). $^1H$ NMR (300 MHz, CHLOROFORM-d) δ ppm 1.45 (s, 9H) 4.58 (br. s., 2H) 7.31 (dd, J=7.93, 1.51 Hz, 1H) 7.43 (t, J=7.93 Hz, 1H) 7.57 (dd, J=8.12, 1.32 Hz, 1H) 7.77 (d, J=1.89 Hz, 1H) 7.93 (dd, J=8.69, 1.89 Hz, 1H) 8.33 (s, 1H) 8.44 (d, J=8.69 Hz, 1H); LC/MS observed [M+H]$^+$ 343.0.

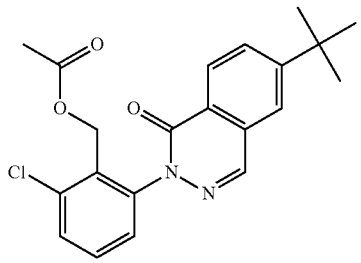 [SMILES: CC(=O)OCc1c(Cl)cccc1-n1ncc2cc(C(C)(C)C)ccc2c1=O]

Acetic acid 2-(6-tert-butyl-1-oxo-1H-phthalazin-2-yl)-6-chloro-benzyl ester

To a solution of 6-tert-butyl-2-(3-chloro-2-(hydroxymethyl)phenyl)phthalazin-1(2H)-one (28.3 g, 82.6 mmol, Eq: 1.00) in dichloromethane (250 ml) was added triethylamine (10.9 g, 10.1 ml, 107 mmol, Eq: 1.3), acetic anhydride (11.0 g, 15.1 ml, 107 mmol, Eq: 1.3), and DMAP (252 mg, 2.06 mmol, Eq: 0.025) and the solution stirred at ambient temperature overnight. The reaction mixture was poured into 300 mL $H_2O$ and extracted with $CH_2Cl_2$ (3×250 mL). The organic layer was dried over sodium sulfate, filtered and concentrated to obtain a semisolid. The semisolid was taken up in 300 mL of isopropyl acetate and was concentrated to afford a slightly yellow solid. This solid was triturated with 150 mL of isopropyl acetate with cooling, followed by filtration and washing once with 30 mL cold isopropyl acetate and then 50 mL 2:1 hexanes: isopropyl acetate to afford acetic acid 2-(6-tert-butyl-1-oxo-1H-phthalazin-2-yl)-6-chloro-benzyl ester (23.9 g) as a white fluffy solid. $^1H$ NMR (300 MHz, CHLOROFORM-d) δ ppm 1.44 (s, 9H) 1.91 (s, 3H) 5.18 (s, 2H) 7.31-7.38 (m, 1H) 7.45 (t, J=7.93 Hz, 1H) 7.51-7.59 (m, 1H) 7.73 (d, J=1.89 Hz, 1H) 7.89 (dd, J=8.69, 1.89 Hz, 1H) 8.25 (s, 1H) 8.40 (d, J=8.69 Hz, 1H). LC/MS observed [M+H]$^+$ 385.0.

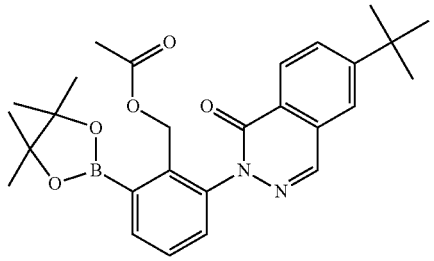 [SMILES: CC(=O)OCc1c(B2OC(C)(C)C(C)(C)O2)cccc1-n1ncc2cc(C(C)(C)C)ccc2c1=O]

Acetic acid 2-(6-tert-butyl-1-oxo-1H-phthalazin-2-yl)-6-(4,4,5,5-tetramethyl-[1,3,2]dioxaborolan-2-yl)-benzyl ester To a 1 L round bottom flask was added 2-(6-tert-butyl-1-oxophthalazin-2(1H)-yl)-6-chlorobenzyl acetate (16.4 g, 42.6 mmol, Eq: 1.00) and bis(pinacolato)diboron (20.6 g, 81.0 mmol, Eq: 1.9). The material was taken up in methyl-THF (300 ml) and stirred for 5 minutes. The mixture was evacuated and back-filled with argon three times before potassium acetate (10.5 g, 107 mmol, Eq: 2.5) was added quickly to avoid moisture. Palladium(II) acetate (239 mg, 1.07 mmol, Eq: 0.025) was added. X-PHOS (1.02 g, 2.13 mmol, Eq: 0.05) was added. The mixture was evacuated and back-filled with argon three times. The orange-yellow mixture was heated to 68° C. (bath temperature) for 1 h. Only a trace of desired product formed after 1 h. The reaction temperature was adjusted to 70° C. The reaction progress was monitored closely by LCMS. The reaction was stirred at this temperature for 9 additional hours after which only a small amount of starting material, a trace of des-Cl byproduct and mostly product could be seen by LCMS analysis and the reaction was still a pale amber color. The reaction was stirred at 70° C. for an additional 1 h to drive the reaction to completion. Color had turned brown. The reaction was allowed to cool to ambient temperature. The reaction mixture was poured into 400 ml H₂O and extracted with EtOAc (3×250 ml). The combined organic extracts were washed with brine, dried (MgSO4), filtered and concentrated in vacuo. The residue was purified using an Analogix purification system with an SF25-600 g column (eluting with 100% hexanes for 15 min., then 0-25% EtOAc/hexanes). Concentration of the center cut of the product peak, isolated by chromatography, afforded 18 g of >95% pure acetic acid 2-(6-tert-butyl-1-oxo-1H-phthalazin-2-yl)-6-(4,4,5,5-tetramethyl-[1,3,2]dioxaborolan-2-yl)-benzyl ester as a yellow foam. ¹H NMR (300 MHz, CHLOROFORM-d) δ ppm 1.34 (s, 12H) 1.44 (s, 9H) 1.87 (s, 3H) 5.30 (br. s., 2H) 7.39-7.57 (m, 2H) 7.72 (d, J=1.51 Hz, 1H) 7.87 (dd, J=8.50, 1.70 Hz, 1H) 7.97 (dd, J=6.42, 2.64 Hz, 1H) 8.24 (s, 1H) 8.40 (d, J=8.31 Hz, 1H). LC/MS observed for major LC peak [M+H]⁺ 477. Note that this material was prepared several times and the purity of the desired product varied from about 50% to about 95%.

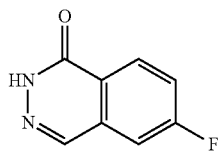

6-Fluoro-2H-phthalazin-1-one

A mixture of N,N-Diethyl-4-fluoro-2-formyl-benzamide (2.94 g, 13.2 mmol), hydrazine monohydrate (Sigma-Aldrich; 725 mg, 14.5 mmol), and EtOH (15 mL) was heated at 50° C. for 45 min in a large capacity microwave tube. Glacial AcOH (2 mL) was added and the mixture was heated at 150° C. for 2 h in a Biotage Initiator microwave. Saturated aqueous NaHCO₃ (75 mL) and EtOAc (70 mL) were added. The organic layer was washed with 5% aqueous NaHCO₃ and then 50% aqueous brine. The aqueous layers were back-extracted with EtOAc (2×60 mL). The combined organic layers were dried (MgSO₄), filtered, and evaporated to give 6-fluoro-2H-phthalazin-1-one (2.14 g, 99%) as a light yellow powder. LC/MS observed [M+H]⁺ 165.

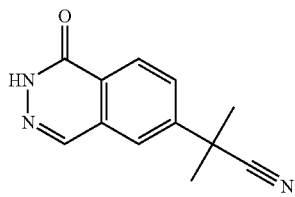 [SMILES: CC(C)(C#N)c1ccc2c(=O)[nH]ncc2c1]

2-Methyl-2-(1-oxo-1,2-dihydro-phthalazin-6-yl)-propionitrile

Potassium bis(trimethylsilyl)amide (0.91 M in THF, Alfa-Aesar; 46.6 mL, 42.4 mmol) was added to a solution of 6-fluoro-2H-phthalazin-1-one (1.16 g, 7.1 mmol) in THF (20 mL). The mixture was heated in an oil-bath overnight at 70° C. Water (125 mL) and EtOAc (100 mL) were added. The layers were separated and the aqueous layer was back-extracted with EtOAc (2×70 mL). The combined organic layers were dried (MgSO₄), filtered, and evaporated to give a yellow solid (1.52 g). This material was purified by trituration with hot CH₂Cl₂/hexanes followed by filtration to give 2-methyl-2-(1-oxo-1,2-dihydro-phthalazin-6-yl)-propionitrile (1.12 g, 74%) as a light yellow powder. LC/MS observed [M+H]⁺ 214.

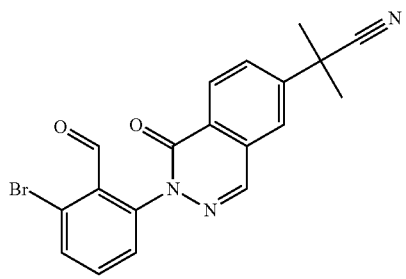 [SMILES: CC(C)(C#N)c1ccc2c(=O)n(-c3cccc(Br)c3C=O)ncc2c1]

2-[2-(3-Bromo-2-formyl-phenyl)-1-oxo-1,2-dihydro-phthalazin-6-yl]-2-methyl-propionitrile A mixture of 2-methyl-2-(1-oxo-1,2-dihydro-phthalazin-6-yl)-propionitrile (1.12 g, 5.23 mmol), 2,6-dibromobenzaldehyde (2.21 g, 8.37 mmol), NaHCO₃ (879 mg, 10.5 mmol), copper(I) iodide (996 mg, 5.23 mmol) and DMSO (35.3 mL) was heated at ~110° C. for 2 h. The mixture was cooled to room temperature. CH₂Cl₂ (40 mL) and water (40 mL) were added. The mixture was filtered through celite and the celite was washed well with CH₂Cl₂ and a small amount of MeOH. The layers in the filtrate were separated and the organic layer was washed with 50% aqueous brine. The aqueous layer was back-extracted with CH₂Cl₂ (2×40 mL). The combined organic layers were dried (MgSO₄), filtered, and concentrated in vacuo. The residue was purified using an Analogix purification system with an SF25-60 g silica column (eluting with 0-5% MeOH/CH₂Cl₂) to give 2-[2-(3-bromo-2-formyl-phenyl)-1-oxo-1,2-dihydro-phthalazin-6-yl]-2-methyl-propionitrile (1.89 mg, 82%) as a light yellow solid with a purity around 90%. LC/MS observed [M+H]⁺ 396/398.

Example 1

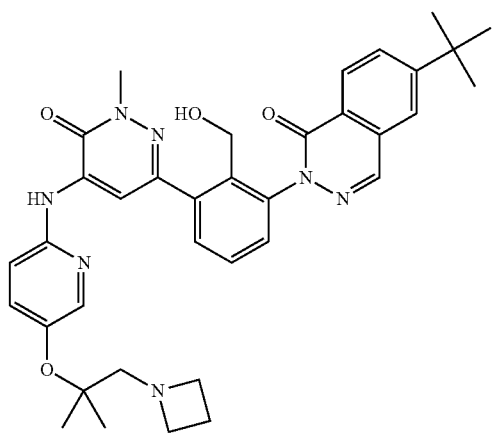 [SMILES: Cn1nc(-c2cccc(-n3ncc4cc(C(C)(C)C)ccc4c3=O)c2CO)cc(Nc2ccc(OC(C)(C)CN3CCC3)cn2)c1=O]

2-(3-{5-[5-(2-Azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-6-tert-butyl-2H-phthalazin-1-one A mixture of acetic acid 2-(6-tert-butyl-1-oxo-1H-phthalazin-2-yl)-6-(4,4,5,5-tetramethyl-[1,3,2]dioxaborolan-2-yl)-benzyl ester (Intermediate 5; 177 mg, 371 µmol), 4-[5-(2-azetidin-1-yl-1,1-dimethyl-ethoxy)-pyridin-2-ylamino]-6-chloro-2-methyl-2H-pyridazin-3-one (which may be prepared as described in Berthel, S. J. et al. US 20120040949 Preparation of 1-13 Step 2; 90 mg, 247 µmol), 2-dicyclohexylphosphino-2',4',6'-triisopropylbiphenyl (18 mg, 37 µmol), potassium phosphate tribasic (144 mg, 0.68 mmol), water (332 µL) and n-butanol (1.4 mL) was degassed by evacuating and back-filling with argon.

Bis(dibenzylideneacetone)palladium(0) (10 mg, 17 µmol) was added and the mixture was degassed as before. The mixture was heated at 110° C. for 2.5 h. Water (35 mL) and EtOAc (35 mL) were added and the mixture was shaken in a separatory funnel. The organic layer was collected and washed with brine (35 mL). The aqueous layers were back-extracted with EtOAc (2×30 mL). The combined organic layers were dried (MgSO$_4$), filtered, evaporated, and purified using an Analogix purification system with a 24 g column (eluting with 1-20% MeOH/CH$_2$Cl$_2$) to give a mixture of acetic acid 2-{5-[5-(2-azetidin-1-yl-1,1-dimethyl-ethoxy)-pyridin-2-ylamino]-1-methyl-6-oxo-1,6-dihydro-pyridazin-3-yl}-6-(6-tert-butyl-1-oxo-1H-phthalazin-2-yl)-benzyl ester and 2-(3-{5-[5-(2-azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-6-tert-butyl-2H-phthalazin-1-one (112 mg) as a viscous light yellow oil. Dioxane (572 µL) and 2 N aqueous NaOH (980 µL, 1.96 mmol) were added and the mixture was heated under argon at 50° C. for 2 h. Water (25 mL) and EtOAc (50 mL) were added and the mixture was shaken in a separatory funnel. The organic layer was collected and washed with brine (50 mL). The aqueous layer was back-extracted with EtOAc (2×40 mL). The combined organic layers were dried (MgSO$_4$), filtered, evaporated, and purified using an Analogix purification system with a 12 g column (eluting with 1-15% MeOH/CH$_2$Cl$_2$) to give 2-(3-{5-[5-(2-azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-6-tert-butyl-2H-phthalazin-1-one (81 mg, 52%) as a light yellow solid. LC/MS observed [M+H]$^+$ 636.0.

Example 2

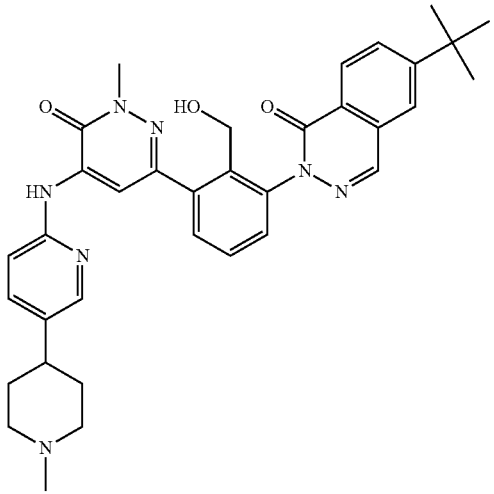 [SMILES: CN1CCC(c2ccc(Nc3cc(-c4cccc(-n5ncc6cc(C(C)(C)C)ccc6c5=O)c4CO)nn(C)c3=O)nc2)CC1]

6-tert-Butyl-2-{2-hydroxymethyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-2H-phthalazin-1-one A mixture of acetic acid 2-(6-tert-butyl-1-oxo-1H-phthalazin-2-yl)-6-(4,4,5,5-tetramethyl-[1,3,2]dioxaborolan-2-yl)-benzyl ester (which may be prepared as described for Example 5; ~75% pure; 214 mg, ~0.34 mmol), 6-chloro-2-methyl-4-(5-(1-methylpiperidin-4-yl)pyridin-2-ylamino)pyridazin-3(2H)-one (which may be prepared as described in Berthel, S. J. et al. US20120040949 Intermediate in Example 56; 100 mg, 0.3 mmol), bis(dibenzylideneacetone) palladium (Aldrich; 8.6 mg, 15 µmol), XPhos (2-(dicyclohexylphosphino)-2',4',6'-tri-i-propyl-1,1'-biphenyl, Strem Chemicals; 14.3 mg, 30 µmol) and potassium phosphate tribasic (159 mg, 0.75 mmol) in a microwave vial was purged and a mixture of degassed n-butanol (2.4 mL) and water (600 µL) was added. The mixture was heated at 115° C. in a sand bath overnight. The mixture was filtered through celite, concentrated, and purified by chromatography (eluting with 0-25% MeOH/CH$_2$Cl$_2$) to give a yellow oil (150 mg). MeOH (2.3 mL) and potassium carbonate (96 mg, 0.7 mmol) were added and the mixture was heated at 45° C. for 1 h. CH$_2$Cl$_2$ was added to improve solubility and the mixture was heated again at 45° C. The mixture was cooled to room temperature and water was added dropwise. The resulting mixture was stirred at room temperature overnight and then extracted with CH$_2$Cl$_2$. The organic extract was concentrated and the residue was triturated with isopropyl acetate. The solid was filtered off, washed with ether, and dried in a vacuum oven for several hours to give 6-tert-butyl-2-{2-hydroxymethyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-2H-phthalazin-1-one (100 mg, 55%) as off-white crystals. NMR showed the presence a small amount of isopropyl acetate. LC/MS observed [M+H]$^+$ 606.1.

Example 3

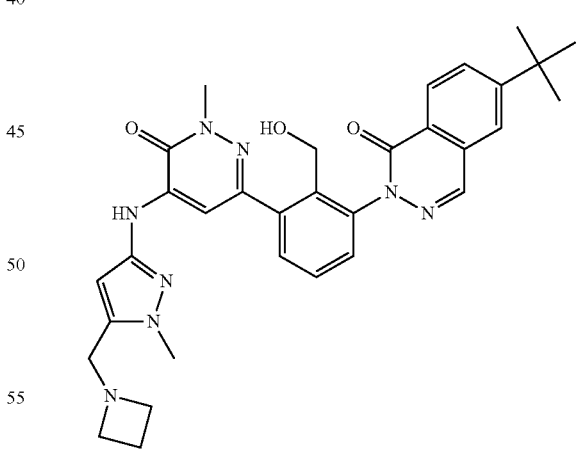

2-{3-[5-(5-Azetidin-1-ylmethyl-1-methyl-1H-pyrazol-3-ylamino)-1-methyl-6-oxo-1,6-dihydro-pyridazin-3-yl]-2-hydroxymethyl-phenyl}-6-tert-butyl-2H-phthalazin-1-one A mixture of acetic acid 2-(6-tert-butyl-1-oxo-1H-phthalazin-2-yl)-6-(4,4,5,5-tetramethyl-[1,3,2]dioxaborolan-2-yl)-benzyl ester (which may be prepared as described for Example 5; ~75% pure; 206 mg, ~0.32 mmol), 4-(5-(azetidin-1-ylmethyl)-1-methyl-1H-pyrazol-3-ylamino)-6-chloro-2-methylpyridazin-3(2H)-one (which may be prepared as described in Berthel, S. J. et al. US20120040949 Intermediate in Example 58; 89 mg, 0.29 mmol), bis(dibenzylideneacetone)palladium (Aldrich; 8.3 mg, 14 µmol), XPhos (2-(dicyclohexylphosphino)-2',4',6'-tri-i-propyl-1,1'-biphenyl, Strem Chemicals; 13.7 mg, 29 µmol), and potassium phosphate tribasic (184 mg, 0.87 mmol) in a microwave vial was purged with nitrogen and a mixture of degassed n-butanol (2.3 mL) and water (576 µL) was added. The mixture was heated at 115° C. in a sand bath overnight. The mixture was evaporated and purified by chromatography (eluting with 0-25% MeOH/CH$_2$Cl$_2$) to give a yellow oil (150 mg). MeOH (2.4 mL) and potassium carbonate (83 mg, 0.6 mmol) were added and the mixture was stirred at room temperature for 1 h. Water was added dropwise and the resulting mixture was stirred at room temperature for 1 h. The solid was filtered off and dried in a vacuum oven overnight to give 2-{3-[5-(5-azetidin-1-ylmethyl-1-methyl-H-pyrazol-3-ylamino)-1-methyl-6-oxo-1,6-dihydro-pyridazin-3-yl]-2-hydroxymethyl-phenyl}-6-tert-butyl-2H-phthalazin-1-one (72 mg, 43%) as an off-white crystalline solid. LC/MS observed [M+H]$^+$ 581.4.

Example 4

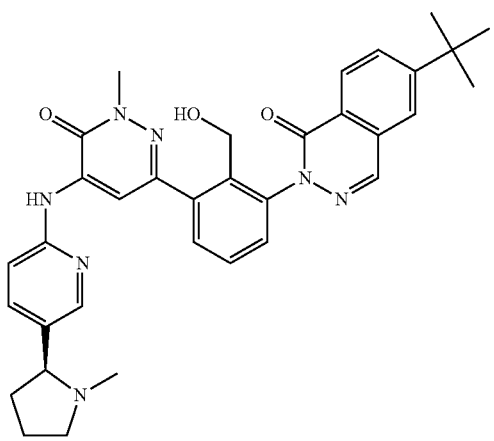 [SMILES: CN1CCC[C@H]1c1ccc(Nc2cc(-c3cccc(-n4ncc5cc(C(C)(C)C)ccc5c4=O)c3CO)nn(C)c2=O)nc1]

6-tert-Butyl-2-(2-hydroxymethyl-3-{1-methyl-5-[5-((S)-1-methyl-pyrrolidin-2-yl)-pyridin-2-ylamino]-6-oxo-1,6-dihydro-pyridazin-3-yl}-phenyl)-2H-phthalazin-1-one A mixture of acetic acid 2-(6-tert-butyl-1-oxo-1H-phthalazin-2-yl)-6-(4,4,5,5-tetramethyl-[1,3,2]dioxaborolan-2-yl)-benzyl ester (which may be prepared as described above; ~75% pure; 172 mg, ~0.27 mmol), (S)-6-chloro-2-methyl-4-(5-(1-methylpyrrolidin-2-yl)pyridin-2-ylamino)pyridazin-3(2H)-one (which may be prepared as described in Berthel, S. J. et al. US20120040949 Example 18 Step 3; 77 mg, 0.24 mmol), bis(dibenzylideneacetone)palladium (Aldrich; 6.9 mg, 12 µmol), XPhos (2-(dicyclohexylphosphino)-2',4',6'-tri-i-propyl-1,1'-biphenyl, Strem Chemicals; 14.3 mg, 30 µmol) and potassium phosphate tribasic (153 mg, 0.72 mmol) in a microwave vial was purged and a mixture of degassed n-butanol (2.4 mL) and water (600 µL) was added. The mixture was heated at 115° C. in a sand bath for 2.5 h. The mixture was filtered through celite, concentrated, and purified by chromatography (eluting with 0-25% MeOH/CH$_2$Cl$_2$) to give a 100 mg of a mixture of products. MeOH (1.58 mL) was added, followed by CH$_2$Cl$_2$ to dissolve the solid. Potassium carbonate (65.4 mg, 0.47 mmol) was added and the mixture was heated at 44° C. for 1.5 h. Water was added dropwise and the mixture was stirred at room temperature for 2 h. The mixture was filtered, and the solid was washed with water and Et$_2$O, and dried in a vacuum over the weekend to give 6-tert-butyl-2-(2-hydroxymethyl-3-{1-methyl-5-[5-((S)-1-methyl-pyrrolidin-2-yl)-pyridin-2-ylamino]-6-oxo-1,6-dihydro-pyridazin-3-yl}-phenyl)-2H-phthalazin-1-one (85 mg, 91%) as an off-white crystalline solid. [M+H]$^+$ 592.5.

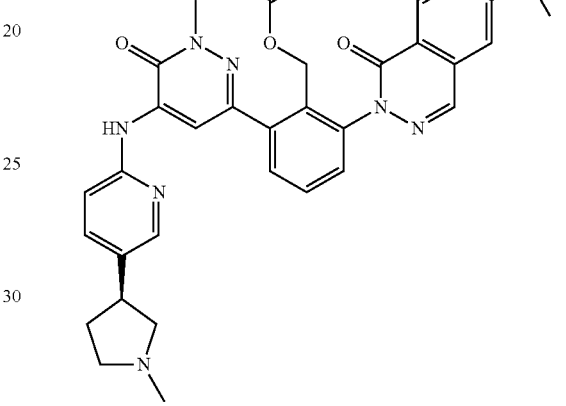

Acetic acid 2-(6-tert-butyl-1-oxo-1H-phthalazin-2-yl)-6-{1-methyl-5-[5-((S)-1-methyl-pyrrolidin-3-yl)-pyridin-2-ylamino]-6-oxo-1,6-dihydro-pyridazin-3-yl}-benzyl ester A mixture of 6-chloro-2-methyl-4-[5-((S)-1-methyl-pyrrolidin-3-yl)-pyridin-2-ylamino]-2H-pyridazin-3-one (which may be prepared as described in Berthel, S. J. et al. US20120040949 Example 32 Step 4; 150 mg, 469 µmol), bis(pinacolato)diboron (155 mg, 610 µmol), potassium acetate (138 mg, 1.41 mmol) and dioxane (7 mL) was degassed under argon. XPhos (2-(dicyclohexylphosphino)-2',4',6'-tri-i-propyl-1,1'-biphenyl, Strem Chemicals; 33.5 mg, 70.4 µmol) and palladium(II) acetate (5.3 mg, 23.5 µmol) were added and the reaction mixture was stirred at 100° C. (external temperature) for 30 min under argon. The flask was raised out of the heating bath and 2-(6-tert-butyl-1-oxophthalazin-2(1H)-yl)-6-chlorobenzyl acetate (Example 4; 199 mg, 516 µmol), potassium carbonate (194 mg, 1.41 mmol), tricyclohexylphosphine (13.2 mg, 46.9 µmol) and bis(dibenzylideneacetone)palladium(0) (13.5 mg, 23.5 µmol), and water (1.5 ml) were added. The reaction mixture was flushed with argon and heated with vigorous stirring at 80° C. for 7 h. The reaction mixture was cooled to room temperature and poured into water and EtOAc. The EtOAc layer was separated and the aqueous layer was extracted with EtOAc. The combined organic layers were washed with brine, dried (Na$_2$SO$_4$), filtered and evaporated. The residue was purified using an Analogix system with a 12 G column (eluting with CH$_2$Cl$_2$/MeOH/NH$_4$OH 89:9:2→66:27:7) to give acetic acid 2-(6-tert-butyl-1-oxo-1H-phthalazin-2-yl)-

6-{1-methyl-5-[5-((S)-1-methyl-pyrrolidin-3-yl)-pyridin-2-ylamino]-6-oxo-1,6-dihydro-pyridazin-3-yl}-benzyl ester (78 mg, 26%). LC/MS observed [M+H]+ 634.

Example 5

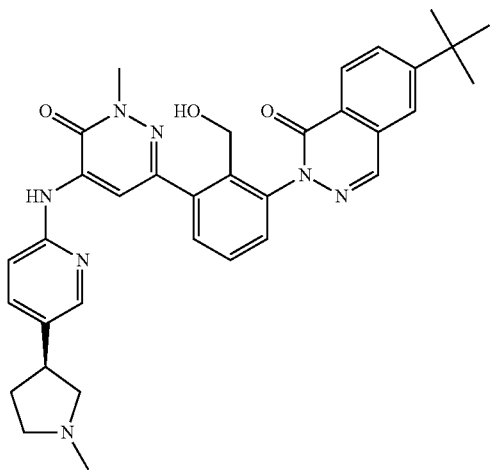 [SMILES: CN1CC[C@@H](c2ccc(Nc3cc(-c4cccc(-n5ncc6cc(C(C)(C)C)ccc6c5=O)c4CO)nn(C)c3=O)nc2)C1]

6-tert-Butyl-2-(2-hydroxymethyl-3-{1-methyl-5-[5-((S)-1-methyl-pyrrolidin-3-yl)-pyridin-2-ylamino]-6-oxo-1,6-dihydro-pyridazin-3-yl}-phenyl)-2H-phthalazin-1-one A mixture of acetic acid 2-(6-tert-butyl-1-oxo-1H-phthalazin-2-yl)-6-{1-methyl-5-[5-((S)-1-methyl-pyrrolidin-3-yl)-pyridin-2-ylamino]-6-oxo-1,6-dihydro-pyridazin-3-yl}-benzyl ester (78 mg, 0.124 mmol), K₂CO₃ (34.2 mg, 0.247 mmol) and MeOH (10 mL) was stirred at 40° C. for 75 min, and then cooled to room temperature. Water and CH₂Cl₂ were added and the aqueous layer was extracted with CH₂Cl₂. The combined organic layers were dried (Na₂SO₄), filtered and evaporated. The residue was triturated with Et₂O and the resulting solid was dried under vacuum overnight to give 6-tert-tutyl-2-(2-hydroxymethyl-3-{1-methyl-5-[5-((S)-1-methyl-pyrrolidin-3-yl)-pyridin-2-ylamino]-6-oxo-1,6-dihydro-pyridazin-3-yl}-phenyl)-2H-phthalazin-1-one (57 mg, 79%) as a yellow solid. LC/MS observed [M+H]+ 592.

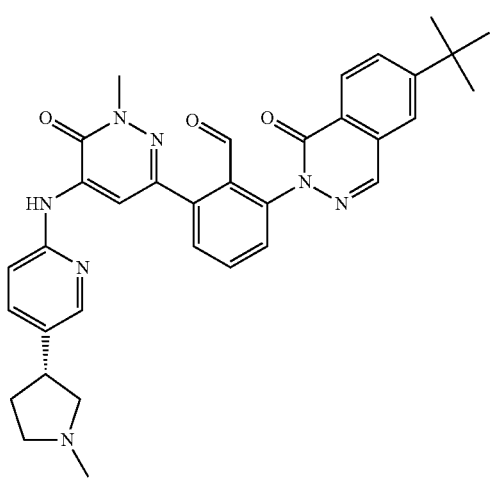 [SMILES: CN1CC[C@H](c2ccc(Nc3cc(-c4cccc(-n5ncc6cc(C(C)(C)C)ccc6c5=O)c4C=O)nn(C)c3=O)nc2)C1]

2-(6-tert-Butyl-1-oxo-1H-phthalazin-2-yl)-6-{1-methyl-5-[5-((R)-1-methyl-pyrrolidin-3-yl)-pyridin-2-ylamino]-6-oxo-1,6-dihydro-pyridazin-3-yl}-benzaldehyde A mixture of 6-chloro-2-methyl-4-[5-((R)-1-methyl-pyrrolidin-3-yl)-pyridin-2-ylamino]-2H-pyridazin-3-one (which may be prepared as described in Berthel, S. J. et al. US20120040949 Example 33 Step 1; 150 mg, 469 µmol), bis(pinacolato)diboron (155 mg, 610 µmol), potassium acetate (138 mg, 1.41 mmol) and dioxane (7 mL) was degassed under argon. XPhos (2-(dicyclohexylphosphino)-2',4',6'-tri-i-propyl-1,1'-biphenyl, Strem Chemicals; 33.5 mg, 70.4 µmol) and palladium(II) acetate (5.3 mg, 23.5 µmol) were added and the reaction mixture was stirred at 100° C. (external temperature) for 30 min under argon. The flask was raised out of the heating bath and 2-(6-tert-butyl-1-oxophthalazin-2(1H)-yl)-6-chlorobenzaldehyde (Example 2; 160 mg, 469 µmol), potassium carbonate (194 mg, 1.41 mmol), tricyclohexylphosphine (13.2 mg, 46.9 µmol) and bis(dibenzylideneacetone)palladium(0) (13.5 mg, 23.5 µmol), and water (1.5 ml) were added. The reaction mixture was flushed with argon and heated with vigorous stirring at 80° C. for 1 h. The reaction mixture was cooled to room temperature and poured into water and EtOAc. The EtOAc layer was separated and the aqueous layer was extracted with EtOAc. The combined organic layers were washed with brine, dried (Na₂SO₄), filtered and evaporated. The residue was purified using an Analogix system with a Supelco 24 G column (eluting with CH₂Cl₂/MeOH/NH₄OH 77:18:5) to give acetic acid 2-(6-tert-butyl-1-oxo-1H-phthalazin-2-yl)-6-{1-methyl-5-[5-((R)-1-methyl-pyrrolidin-3-yl)-pyridin-2-ylamino]-6-oxo-1,6-dihydro-pyridazin-3-yl}-benzyl ester (16 mg, 6%). LC/MS observed [M+H]+ 633.9.

Example 6

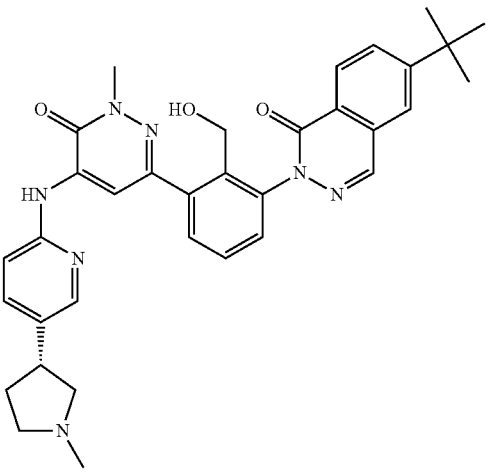 [SMILES: CN1CC[C@H](c2ccc(Nc3cc(-c4cccc(-n5ncc6cc(C(C)(C)C)ccc6c5=O)c4CO)nn(C)c3=O)nc2)C1]

6-tert-Butyl-2-(2-hydroxymethyl-3-{1-methyl-5-[5-((R)-1-methyl-pyrrolidin-3-yl)-pyridin-2-ylamino]-6-oxo-1,6-dihydro-pyridazin-3-yl}-phenyl)-2H-phthalazin-1-one Preparation of 6-tert-butyl-2-(2-hydroxymethyl-3-{1-methyl-5-[5-((R)-1-methyl-pyrrolidin-3-yl)-pyridin-2-ylamino]-6-oxo-1,6-dihydro-pyridazin-3-yl}-phenyl)-2H-phthalazin-1-one A mixture of acid 2-(6-tert-butyl-1-oxo-1H-phthalazin-2-yl)-6-{1-methyl-5-[5-((R)-1-methyl-pyrrolidin-3-yl)-pyridin-2-ylamino]-6-oxo-1,6-dihydro-pyridazin-3-yl}-benzyl ester (16 mg, 27 µmol), sodium borohydride (1.64 mg, 43.4

μmol), and methanol (1 mL) was stirred under nitrogen for 30 min. Saturated aqueous NH₄Cl was added and the mixture was stirred for 5 min and then extracted twice with CH₂Cl₂. The combined organic layers were dried, filtered, and evaporated. The residue was purified by column chromatography (eluting with CH₂Cl₂/MeOH/NH₄OH 89:9:2→66:27:7) and the product was dried in a vacuum oven overnight at 50° C. to give 6-tert-butyl-2-(2-hydroxymethyl-3-{1-methyl-5-[5-((R)-1-methyl-pyrrolidin-3-yl)-pyridin-2-ylamino]-6-oxo-1,6-dihydro-pyridazin-3-yl}-phenyl)-2H-phthalazin-1-one (11.8 mg, 74%) as a light yellow solid. LC/MS observed [M+H]⁺ 592.

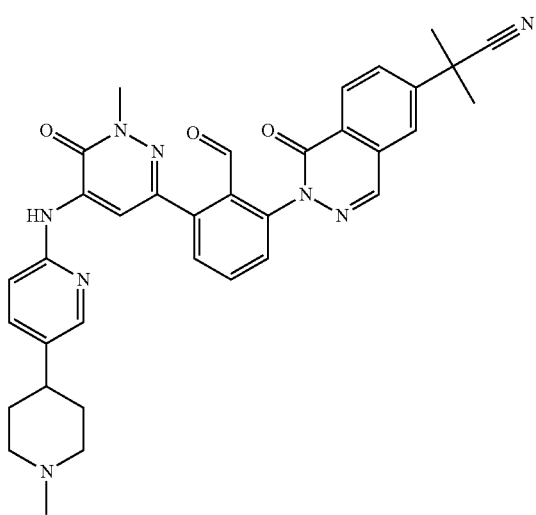 [SMILES: CN1CCC(c2ccc(Nc3cc(-c4cccc(-n5ncc6cc(C(C)(C)C#N)ccc6c5=O)c4C=O)nn(C)c3=O)nc2)CC1]

2-(2-{2-Formyl-3-[1-methyl-5-(1'-methyl-1',2',3',4', 5',6'-hexahydro-[3,4']bipyridinyl-6-ylamino)-6-oxo-1,6-dihydro-pyridazin-3-yl]-phenyl}-1-oxo-1,2-dihydro-phthalazin-6-yl)-2-methyl-propionitrile Solution A was prepared as follows: A mixture of 6-chloro-2-methyl-4-(5-(1-methylpiperidin-4-yl)pyridin-2-ylamino)pyridazin-3(2H)-one (which may be made as described in Berthel, S. J. et al. US20120040949 Preparation of I-67 Step 2; 125 mg, 0.374 mmol), XPhos (2-(dicyclohexylphosphino)-2',4',6'-tri-i-propyl-1,1'-biphenyl, Strem Chemicals; 27 mg, 56 μmol), potassium acetate (110 mg, 1.1 mmol), bis(pinacolato)diboron (124 mg, 0.49 mmol), and dioxane (4.4 mL) was vacuum-degassed under reduced pressure and placed under an argon atmosphere. Palladium (II) acetate (9.25 mg, 41.2 μmol) was added at room temperature and the vacuum-degas cycle was repeated. The reaction mixture was stirred at 100° C. (external temperature) under argon for 16 min. The reaction mixture was cooled to ambient temperature and filtered through a plug of celite using argon pressure (washing the celite with an additional 2.5 mL of dioxane) to give solution A.

Solution B was prepared as follows: A mixture of 2-(2-(3-bromo-2-formylphenyl)-1-oxo-1,2-dihydrophthalazin-6-yl)-2-methylpropanenitrile (Example 8; 158 mg, 399 μmol), tricyclohexylphosphine (34.2 mg, 122 μmol), K2CO3 (276 mg, 2 mmol), n-BuOH (486 μL), water (1.52 mL), and dioxane (2.03 mL) was degassed. Bis(dibenzylideneacetone)palladium(0) (34.4 mg, 59.8 μmol) was added at room temperature. The mixture was vacuum degassed again, and then heated in a heating bath set to 110° C.

SOLUTION A was added to SOLUTION B and the resulting mixture was stirred for 35 min at 110° C. The heating was turned off and the reaction mixture was allowed to stir overnight. The reaction mixture was filtered through celite and the celite was washed with EtOAc. EtOAc (30 mL) and water (30 mL) were added to the filtrate and the filtrate was shaken in a separatory funnel. The EtOAc phase was collected. The aqueous layer was back-extracted with EtOAc (2×20 mL) and the combined organic layers were dried (Na₂SO₄), filtered, and evaporated. The residue was purified by chromatography using an Analogix system with an SF15-24 g column (eluting with 3-18% MeOH/CH₂Cl₂) to give 2-(2-{2-formyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-1-oxo-1,2-dihydro-phthalazin-6-yl)-2-methyl-propionitrile (178 mg, 73%) as a grey powder. LC/MS observed [M+H]⁺ 615.

Example 7

2-(2-{2-hydroxymethyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-1-oxo-1,2-dihydro-phthalazin-6-yl)-2-methyl-propionitrile

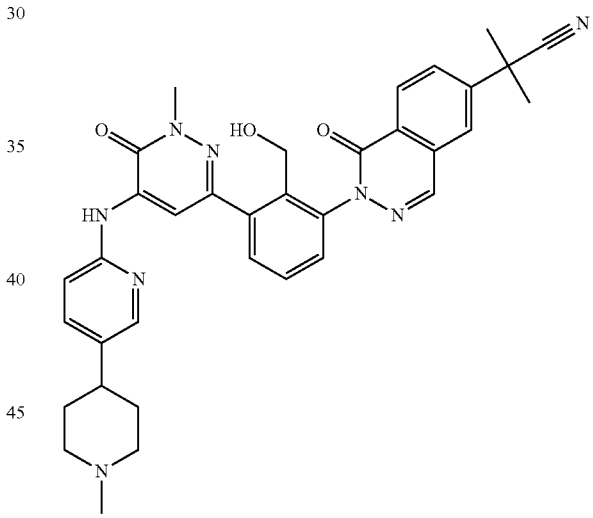

A mixture of 2-(2-{2-formyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-1-oxo-1,2-dihydro-phthalazin-6-yl)-2-methyl-propionitrile (Example 17; 178 mg, 0.29 mmol) was taken up in MeOH (4 mL) and CH₂Cl₂ (2.3 mL) and cooled to 0° C. A solution of NaBH4 (55 mg, 1.5 mmol) in water (0.5 mL) was added dropwise and the mixture stirred for 10 minutes. Then extra NaBH₄ (55 mg, 1.5 mmol) in water (0.5 mL) was added and the mixture was stirred for an additional 10 minutes. Water (60 mL) and CH₂Cl₂ (60 mL) were added and the material was shaken in a separatory funnel. The organic layer was collected and washed with a 50% diluted brine solution and the aqueous phases were back-extracted with CH₂Cl₂ (2×40 mL). The combined organic layers were dried (MgSO₄), filtered and evaporated. The residue was purified using an Analogix purification system with an SF15-12G silica column (eluting with 3-14% MeOH/CH$_2$Cl$_2$) to give a light yellow solid (138 mg). This was recrystallized from CH$_2$Cl$_2$/hexanes to give 2-(2-{2-hydroxymethyl-3-[1-methyl-5-(1'-methyl-1',2', 3',4',5',6'-hexahydro-[3,4']bipyridinyl-6-ylamino)-6-oxo-1, 6-dihydro-pyridazin-3-yl]-phenyl}-1-oxo-1,2-dihydro-phthalazin-6-yl)-2-methyl-propionitrile (109 mg, 61%) as white crystals. LC/MS observed [M+H]$^+$ 617.

Example 8

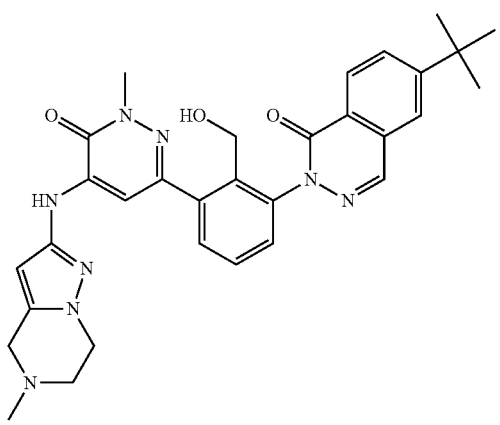 [SMILES: CN1CCn2nc(Nc3cc(-c4cccc(-n5ncc6cc(C(C)(C)C)ccc6c5=O)c4CO)nn(C)c3=O)cc2C1]

6-tert-Butyl-2-{2-hydroxymethyl-3-[1-methyl-5-(5-methyl-4,5,6,7-tetrahydro-pyrazolo[1,5-a]pyrazin-2-ylamino)-6-oxo-1,6-dihydro-pyridazin-3-yl]-phenyl}-2H-phthalazin-1-one A degassed mixture of n-BuOH (4 mL) and water (1 mL) was added to a mixture of acetic acid 2-(6-tert-butyl-1-oxo-1H-phthalazin-2-yl)-6-(4,4,5,5-tetramethyl-[1,3,2]dioxaborolan-2-yl)-benzyl ester (which may be prepared as described for Example 5; ~75% pure; 364 mg, ~0.57 mmol), 6-chloro-2-methyl-4-(5-methyl-4,5,6,7-tetrahydro-pyrazolo [1,5-a]pyrazin-2-ylamino)-2H-pyridazin-3-one (which may be prepared as described in Berthel, S. J. et al. US20120040949 Intermediate in the preparation of Example 59; 150 mg, 0.51 mmol), bis(dibenzylideneacetone)palladium (Aldrich; 14.6 mg, 25 μmol), XPhos (2-(dicyclohexylphosphino)-2',4',6'-tri-i-propyl-1,1'-biphenyl, Strem Chemicals; 24.3 mg, 51 μmol), and potassium phosphate tribasic (324 mg, 1.5 mmol) in a microwave vial. The vial was capped and the mixture was heated at 115° C. in a sand bath for 2.5 h. The mixture was filtered through celite, evaporated and purified by chromatography (eluting with 0-25% MeOH/CH$_2$Cl$_2$) to give 175 mg of a mixture of products. MeOH (2.9 mL) and potassium carbonate (119 mg, 0.86 mmol) were added and the mixture was stirred at 40° C. for 1 h. Water was added dropwise and the resulting mixture was stirred at room temperature for 1 h. Water was added dropwise and the mixture was stirred at room temperature for 1 h. The resulting solid was filtered off and dried in a vacuum oven overnight to give 6-tert-butyl-2-{2-hydroxymethyl-3-[1-methyl-5-(5-methyl-4,5,6,7-tetrahydro-pyrazolo[1,5-a]pyrazin-2-ylamino)-6-oxo-1,6-dihydro-pyridazin-3-yl]-phenyl}-2H-phthalazin-1-one (147 mg, 51%) as a white crystalline solid. LC/MS observed [M+H]$^+$ 567.0.

Example 9

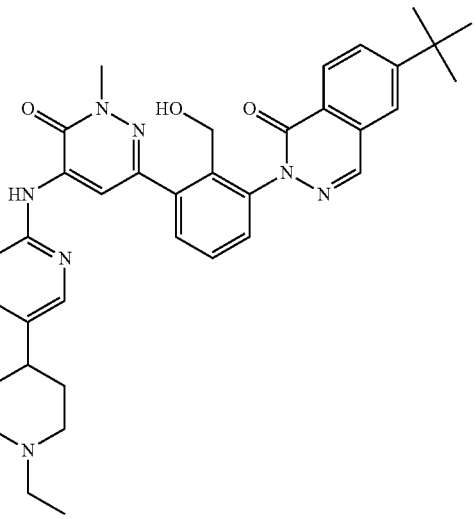

6-tert-Butyl-2-{3-[5-(1'-ethyl-1',2',3',4',5',6'-hexahydro-[3,4']bipyridinyl-6-ylamino)-1-methyl-6-oxo-1,6-dihydro-pyridazin-3-yl]-2-hydroxymethyl-phenyl}-2H-phthalazin-1-one Argon was bubbled through mixture of 6-chloro-4-(1'-ethyl-1',2',3',4',5',6'-hexahydro-[3,4']bipyridinyl-6-ylamino)-2-methyl-2H-pyridazin-3-one (which may be made as described in Berthel, S. J. et al. US20120040949 intermediate in Example 69; 133 mg, 0.38 mmol), 2-(6-tert-butyl-1-oxophthalazin-2(1H)-yl)-6-(4,4,5,5-tetramethyl-1, 3,2-dioxaborolan-2-yl)benzyl acetate (which may be prepared as described for Example 5; ~75% pure; 242 mg, 381 μmol) and potassium phosphate tribasic (202 mg, 953 μmol), water (1.25 mL) and nBuOH (5 mL) for 5 min. XPhos (2-(dicyclohexylphosphino)-2',4',6'-tri-i-propyl-1,1'-biphenyl, Strem Chemicals; 18.2 mg, 38 μmol) and bis(dibenzylideneacetone)palladium(0) (Strem Chemicals; 11.0 mg, 19.1 μmol) were added. The tube was sealed and the reaction mixture was heated at 115° C. for 6 h. The reaction mixture was poured into water (100 mL) and the mixture was extracted with EtOAc (3×75 mL). The combined organic layers were washed with brine, dried (MgSO$_4$), filtered, and evaporated. The residue was purified by chromatography (eluting with 0-6% MeOH/CH$_2$Cl$_2$ and then with NH$_4$OH/ MeOH/CH$_2$Cl$_2$ 4:14:82) and then triturated with EtOAc/ Et$_2$O to give 6-tert-butyl-2-{3-[5-(1'-ethyl-1',2',3',4',5',6'-hexahydro-[3,4']bipyridinyl-6-ylamino)-1-methyl-6-oxo-1, 6-dihydro-pyridazin-3-yl]-2-hydroxymethyl-phenyl}-2H-phthalazin-1-one (32 mg, 13%) as an off-white solid. 1H NMR showed the presence of <3% of an impurity, acetic acid 2-(6-tert-butyl-1-oxo-1H-phthalazin-2-yl)-6-[5-(1'-ethyl-1',2',3',4',5',6'-hexahydro-[3,4']bipyridinyl-6-ylamino)-1-methyl-6-oxo-1,6-dihydro-pyridazin-3-yl]-benzyl ester. LC/MS observed [M+H]$^+$ 620.1.

Example 10

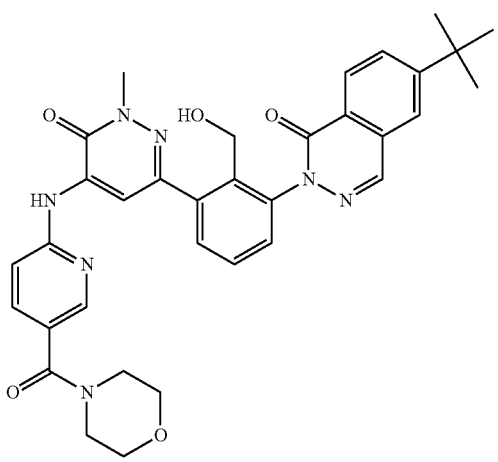 [SMILES: Cn1nc(-c2cccc(-n3ncc4cc(C(C)(C)C)ccc4c3=O)c2CO)cc(Nc2ccc(C(=O)N3CCOCC3)cn2)c1=O]

6-tert-Butyl-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-2H-phthalazin-1-one A degassed mixture of n-BuOH (2.29 mL) and water (0.57 mL) was added to a mixture of acetic acid 2-(6-tert-butyl-1-oxo-1H-phthalazin-2-yl)-6-(4,4,5,5-tetramethyl-[1,3,2]dioxaborolan-2-yl)-benzyl ester (which may be prepared as described for Example 5; ~75% pure; 204 mg, ~0.32 mmol), 6-chloro-2-methyl-4-[5-(morpholine-4-carbonyl)-pyridin-2-ylamino]-2H-pyridazin-3-one (which may be prepared as described in Berthel, S. J. et al. US20120040949 Preparation of I-2; 100 mg, 0.29 mmol), bis(dibenzylideneacetone)palladium (8.2 mg, 14.3 µmol), XPhos (2-(dicyclohexylphosphino)-2',4',6'-tri-i-propyl-1,1'-biphenyl, Strem Chemicals; 13.6 mg, 28.6 µmol), and potassium phosphate tribasic (152 mg, 0.72 mmol) in a microwave vial. The mixture was heated at 115° C. in a sand bath for overnight. The mixture was filtered through celite, evaporated and purified by chromatography (eluting with 0-20% MeOH/CH$_2$Cl$_2$) to give a solid. Methanol was added and the mixture was filtered and dried in a vacuum oven over the weekend to give 6-tert-butyl-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-2H-phthalazin-1-one (46 mg, 26%) as a white powder. LC/MS observed [M+H]$^+$ 622.4.

2-[2-(3-{5-[5-(2-Azetidin-1-yl-1,1-dimethyl-ethoxy)-pyridin-2-ylamino]-1-methyl-6-oxo-1,6-dihydro-pyridazin-3-yl}-2-formyl-phenyl)-1-oxo-1,2-dihydro-phthalazin-6-yl]-2-methyl-propionitrile SOLUTION A was prepared as follows: A mixture of 4-[5-(2-azetidin-1-yl-1,1-dimethyl-ethoxy)-pyridin-2-ylamino]-6-chloro-2-methyl-2H-pyridazin-3-one (which may be prepared as described in Berthel, S. J. et al. US20120040949 Preparation of I-13 Step 2; 150 mg, 0.41 mmol), XPhos (2-(dicyclohexylphosphino)-2',4',6'-tri-i-propyl-1,1'-biphenyl, Strem Chemicals; 29.5 mg, 62 µmol), potassium acetate (121 mg, 1.2 mmol), bis(pinacolato)diboron (Matrix Scientific; 136 mg, 0.54 mmol), and dioxane (5.3 mL) was vacuum-degassed under reduced pressure and placed under an argon atmosphere. Palladium(II) acetate (10.2 mg, 45 µmol) was added at room temperature and the vacuum-degas cycle was repeated. The reaction mixture was stirred at 100° C. (oil bath temperature) under argon for 16 min. The reaction mixture was filtered through a plug of celite using argon pressure (washing the celite with an additional 2.5 mL of dioxane) to give SOLUTION A.

SOLUTION B was prepared as follows: A mixture of 2-(2-(3-bromo-2-formylphenyl)-1-oxo-1,2-dihydrophthalazin-6-yl)-2-methylpropanenitrile (Example 8; 156 mg, 394 µmol), tricyclohexylphosphine (33.8 mg, 120 µmol), K2CO3 (276 mg, 2 mmol), n-BuOH (480 µL), water (1.5 mL), and dioxane (2 mL) was degassed. Bis(dibenzylideneacetone)palladium(0) (34 mg, 59 µmol) was added at room temperature. The mixture was vacuum degassed again, and then heated in an oil bath set to 110° C.

SOLUTION A was added to SOLUTION B and the resulting mixture was stirred for 60 min at 110° C. The reaction mixture was cooled to room temperature and filtered through celite. The celite was washed with EtOAc. EtOAc (30 mL) and water (30 mL) were added to the filtrate and the EtOAc phase was collected. The aqueous layer was back-extracted with EtOAc (2×20 mL) and the combined organic layers were dried (Na$_2$SO$_4$), filtered, and evaporated. The residue was purified by chromatography using an Analogix system with an SF15-12 g column (eluting with 3-18% MeOH/CH$_2$Cl$_2$) to give 2-[2-(3-{5-[5-(2-azetidin-1-yl-1,1-dimethyl-ethoxy)-pyridin-2-ylamino]-1-methyl-6-oxo-1,6-dihydro-pyridazin-3-yl}-2-formyl-phenyl)-1-oxo-1,2-dihydro-phthalazin-6-yl]-2-methyl-propionitrile (201 mg, 79%) as a light brown powder. LC/MS observed [M+H]$^+$ 645.0.

Example 11

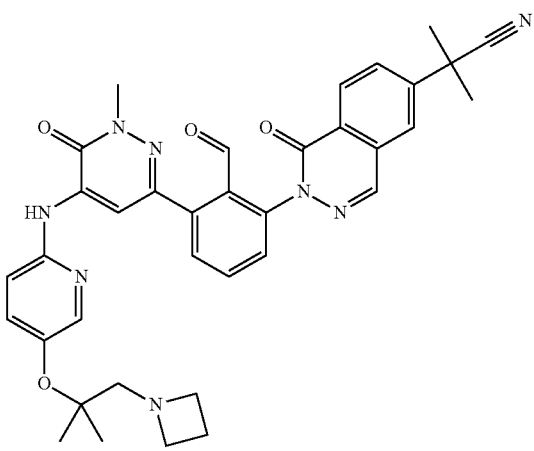 [SMILES: Cn1nc(-c2cccc(-n3ncc4cc(C(C)(C)C#N)ccc4c3=O)c2C=O)cc(Nc2ccc(OC(C)(C)CN3CCC3)cn2)c1=O]

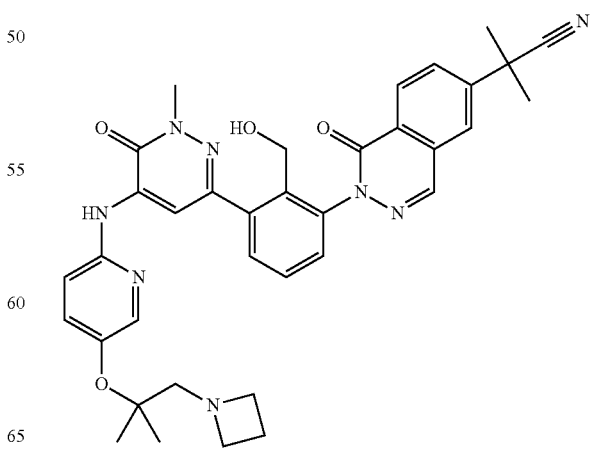

2-[2-(3-{5-[5-(2-Azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-1-oxo-1,2-dihydro-phthalazin-6-yl]-2-methyl-propionitrile To a mixture of 2-{5-[5-(2-azetidin-1-yl-1,1-dimethyl-ethoxy)-pyridin-2-ylamino]-1-methyl-6-oxo-1,6-dihydro-pyridazin-3-yl}-6-(6-tert-butyl-1-oxo-1H-phthalazin-2-yl)-benzaldehyde (201 mg, 0.31 mmol), in MeOH (4.5 mL) and CH$_2$Cl$_2$ (2.3 mL) was added a solution of NaBH$_4$ (59 mg, 1.6 mmol) in water (0.5 mL) by dropwise addition and the resulting mixture was stirred for 10 min at 0° C. A solution of NaBH$_4$ (59 mg, 1.6 mmol) in water (0.5 mL) was added and the mixture was stirred for an additional 10 min. Water (60 mL) and CH$_2$Cl$_2$ (60 mL) were added and the layers separated. The organic layer was washed with 50% aqueous brine (60 mL) and the combined aqueous solutions were back-extracted with CH$_2$Cl$_2$ (2×40 mL). The combined organic layers were dried (MgSO$_4$), filtered and evaporated. The residue was purified using an Analogix purification system with an SF15-12G column (eluting with 2-14% MeOH/CH$_2$Cl$_2$), followed by recrystallization from CH$_2$Cl$_2$/hexanes to give 2-[2-(3-{5-[5-(2-azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-1-oxo-1,2-dihydro-phthalazin-6-yl]-2-methyl-propionitrile (145 mg, 72%) as white crystals. LC/MS observed [M+H]$^+$ 647.1.

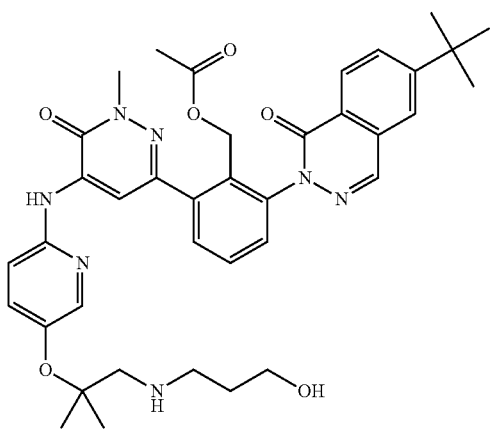 [SMILES: CC(=O)OCc1c(-c2cc(Nc3ccc(OC(C)(C)CNCCCO)cn3)c(=O)n(C)n2)cccc1-n1ncc2cc(C(C)(C)C)ccc2c1=O]

Acetic acid 2-(6-tert-butyl-1-oxo-1H-phthalazin-2-yl)-6-(5-{5-[2-(3-hydroxy-propylamino)-1,1-dimethyl-ethoxy]-pyridin-2-ylamino}-1-methyl-6-oxo-1,6-dihydro-pyridazin-3-yl)-benzyl ester A mixture of 4-[5-(2-azetidin-1-yl-1,1-dimethyl-ethoxy)-pyridin-2-ylamino]-6-chloro-2-methyl-2H-pyridazin-3-one (which may be prepared as described in Berthel, S. J. et al. US20120040949 Preparation of 1-13 Step 2; 1.50 g, 4.12 mmol), acetic acid 2-(6-tert-butyl-1-oxo-1H-phthalazin-2-yl)-6-(4,4,5,5-tetramethyl-[1,3,2]dioxaborolan-2-yl)-benzyl ester (ELN003987-149; 83% pure; 2.95 g, 5.14 mmol), bis(dibenzylideneacetone)palladium (Strem Chemicals; 119 mg, 0.21 mmol), XPhos (2-(dicyclohexylphosphino)-2',4',6'-tri-i-propyl-1,1'-biphenyl, Strem Chemicals; 197 mg, 0.41 mmol), and potassium phosphate tribasic (2.19 g, 10.3 mmol), nBuOH (33 mL) and water (8.25 mL) was flushed with argon and then heated at 100° C. overnight. The mixture was filtered through celite and concentrated. The residue was purified using an Analogix purification system (eluting with CH$_2$Cl$_2$ to CH$_2$Cl$_2$/MeOH/NH$_4$OH (82:14:4)). The pump from the purification system started to malfunction during the purification. The product was eluted from the column using a different Analogix purification system using as eluent CH$_2$Cl$_2$/MeOH/NH$_4$OH (82:14:4→55:36:9)). The product was slurried/dissolved in Et$_2$O/EtOAc (2:1) and the mixture was allowed to sit for 48 h. The solid was filtered to give acetic acid 2-(6-tert-butyl-1-oxo-1H-phthalazin-2-yl)-6-(5-{5-[2-(3-hydroxy-propylamino)-1,1-dimethyl-ethoxy]-pyridin-2-ylamino}-1-methyl-6-oxo-1,6-dihydro-pyridazin-3-yl)-benzyl ester (525 mg, 19%) as a light yellow solid. LC/MS observed [M+H]$^+$ 696.0.

Example 12

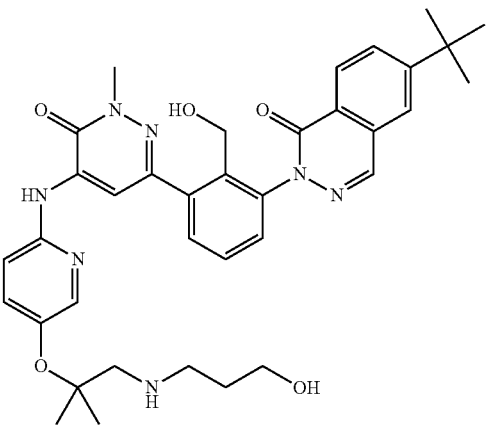 [SMILES: Cn1nc(-c2cccc(-n3ncc4cc(C(C)(C)C)ccc4c3=O)c2CO)cc(Nc2ccc(OC(C)(C)CNCCCO)cn2)c1=O]

6-tert-Butyl-2-[2-hydroxymethyl-3-(5-{5-[2-(3-hydroxy-propylamino)-1,1-dimethyl-ethoxy]-pyridin-2-ylamino}-1-methyl-6-oxo-1,6-dihydro-pyridazin-3-yl)-phenyl]-2H-phthalazin-1-one A mixture of acetic acid 2-(6-tert-butyl-1-oxo-1H-phthalazin-2-yl)-6-(5-{5-[2-(3-hydroxy-propylamino)-1,1-dimethyl-ethoxy]-pyridin-2-ylamino}-1-methyl-6-oxo-1,6-dihydro-pyridazin-3-yl)-benzyl ester (Example 24; 295 mg, 0.42 mmol), K$_2$CO$_3$ (117 mg, 0.85 mmol) and MeOH (30 mL) was stirred at 40° C. for 75 min, and then cooled to room temperature. Water and CH$_2$Cl$_2$ were added and the aqueous layer was extracted with CH$_2$Cl$_2$. The combined organic layers were dried (Na$_2$SO$_4$), filtered and evaporated. The residue was purified by chromatography using a 12 g Silicycle column (eluting with 1-15% MeOH/CH$_2$Cl$_2$). Samples homogeneous for the product were evaporated and the residue was dried under vacuum at 50° C. to give 6-tert-butyl-2-[2-hydroxymethyl-3-(5-{5-[2-(3-hydroxy-propylamino)-1,1-dimethyl-ethoxy]-pyridin-2-ylamino}-1-methyl-6-oxo-1,6-dihydro-pyridazin-3-yl)-phenyl]-2H-phthalazin-1-one (119 mg, 43%) as a light yellow foam. LC/MS observed [M+H]$^+$ 654.2.

Example 13

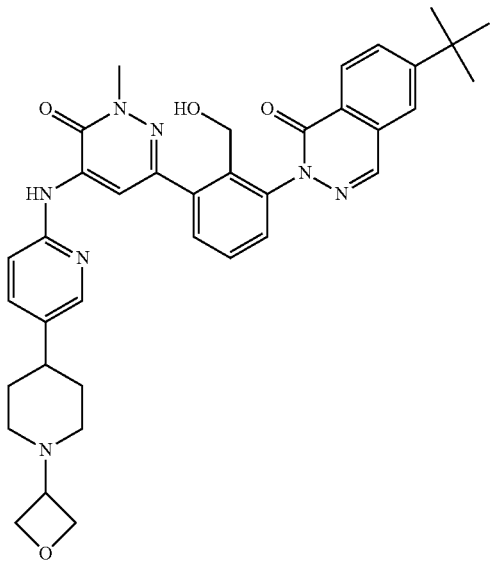 [SMILES: Cn1nc(-c2cccc(-n3ncc4cc(C(C)(C)C)ccc4c3=O)c2CO)cc(Nc2ccc(C3CCN(C4COC4)CC3)cn2)c1=O]

6-tert-Butyl-2-{2-hydroxymethyl-3-[1-methyl-5-(1'-oxetan-3-yl-1',2',3',4',5',6'-hexahydro-[3,4']bipyridinyl-6-ylamino)-6-oxo-1,6-dihydro-pyridazin-3-yl]-phenyl}-2H-phthalazin-1-one Argon was bubbled through mixture of 6-chloro-2-methyl-4-(1'-oxetan-3-yl-1',2',3',4',5',6'-hexahydro-[3,4']bipyridinyl-6-ylamino)-2H-pyridazin-3-one (which may be prepared as described in Berthel, S. J. et al. US20120040949 Example 80 Step 1; 213 mg, 567 μmol), acetic acid 2-(6-tert-butyl-1-oxo-1H-phthalazin-2-yl)-6-(4,4,5,5-tetramethyl-[1,3,2]dioxaborolan-2-yl)-benzyl ester (which may be prepared as described for Example 5; ~75% pure; 648 mg, ~1.0 mmol) and potassium phosphate tribasic (301 mg, 1.42 mmol), water (1.25 mL) and nBuOH (5 mL) for 5 min. XPhos (2-(dicyclohexylphosphino)-2',4',6'-tri-i-propyl-1,1'-biphenyl, Strem Chemicals; 27 mg, 57 μmol) and bis(dibenzylideneacetone)palladium(0) (Strem Chemicals; 16.3 mg, 28 μmol) were added. The tube was sealed and the reaction mixture was heated at 115° C. for 4 h. The reaction mixture was poured into water (100 mL) and the mixture was extracted with CH$_2$Cl$_2$ (5×75 mL). The combined organic layers were washed with brine, dried (Na$_2$SO$_4$), filtered, and evaporated. The residue was purified by chromatography (eluting with 0-4% MeOH/CH$_2$Cl$_2$) to give a mixture of alcohol and acetate products (374 mg). THF (12 mL) and 1 N NaOH (2 mL) were added and the mixture was heated at 60° C. overnight. The mixture was poured into water and extracted three times with EtOAc and once with CH$_2$Cl$_2$. The organic extract was washed with brine, dried (Na$_2$SO$_4$), filtered, and evaporated. The residue was purified by chromatography (eluting with 1-5% MeOH/CH$_2$Cl$_2$) to give a glass. EtOAc (4 mL) and Et$_2$O (30 mL) were added and the white precipitate was filtered off and washed with ether to give 6-tert-butyl-2-{2-hydroxymethyl-3-[1-methyl-5-(1'-oxetan-3-yl-1',2',3',4',5',6'-hexahydro-[3,4']bipyridinyl-6-ylamino)-6-oxo-1,6-dihydro-pyridazin-3-yl]-phenyl}-2H-phthalazin-1-one (246 mg, 67%) as a white powder. LC/MS observed [M+H]$^+$ 648.1.

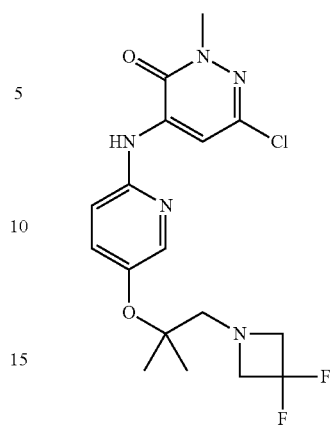

6-Chloro-4-{5-[2-(3,3-difluoro-azetidin-1-yl)-1,1-dimethyl-ethoxy]-pyridin-2-ylamino}-2-methyl-2H-pyridazin-3-one A mixture of 2-[6-(6-chloro-2-methyl-3-oxo-2,3-dihydro-pyridazin-4-ylamino)-pyridin-3-yloxy]-2-methyl-propionaldehyde (which may be prepared as described in Berthel, S. J. et al. US20120040949 Preparation of 1-13 Step 1; 665 mg, 2.06 mmol), 3,3-difluoroazetidin hydrochloride (347 mg, 2.68 mmol), and 1,2-dichloroethane (70 mL) was stirred at room temperature for 1 h. Sodium triacetoxyborohydride (655 mg, 3.09 mmol) was added and the mixture was stirred at room temperature for 18 h. Saturated aqueous NaHCO$_3$ was added and the mixture was extracted with CH$_2$Cl$_2$ (5×20 mL). The combined organic layers were dried (MgSO$_4$), filtered, and evaporated. The residue was purified by chromatography (30-50% EtOAc/hexanes) to give 6-chloro-4-{5-[2-(3,3-difluoro-azetidin-1-yl)-1,1-dimethyl-ethoxy]-pyridin-2-ylamino}-2-methyl-2H-pyridazin-3-one (566 mg, 69%) as a white powder. LC/MS observed [M+H]$^+$ 400.0.

Example 14

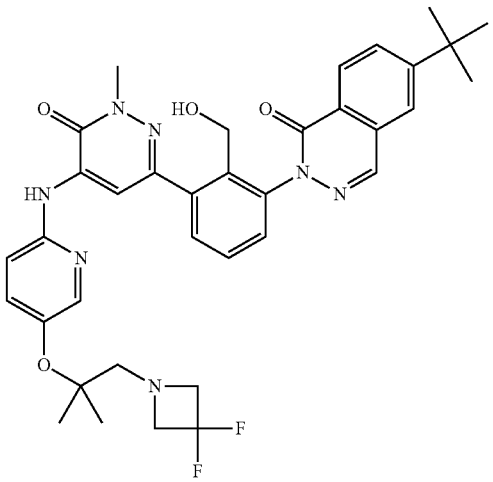 [SMILES: Cn1nc(-c2cccc(-n3ncc4cc(C(C)(C)C)ccc4c3=O)c2CO)cc(Nc2ccc(OC(C)(C)CN3CC(F)(F)C3)cn2)c1=O]

6-tert-Butyl-2-[3-(5-{5-[2-(3,3-difluoro-azetidin-1-yl)-1,1-dimethyl-ethoxy]-pyridin-2-ylamino}-1-methyl-6-oxo-1,6-dihydro-pyridazin-3-yl)-2-hydroxymethyl-phenyl]-2H-phthalazin-1-one A mixture of 6-chloro-4-{5-[2-(3,3-difluoro-azetidin-1-yl)-1,1-dimethyl-ethoxy]-pyridin-2-ylamino}-2-methyl-2H-pyridazin-3-one (Example 27; 120 mg, 0.3 mmol), acetic acid 2-(6-tert-butyl-1-oxo-1H-phthalazin-2-yl)-6-(4,4,5,5-tetramethyl-[1,3,2]dioxaborolan-2-yl)-benzyl ester (which may be prepared as described for Example 5; 310 mg, 0.39 mmol), potassium phosphate tribasic (140 mg, 0.66 mmol), nBuOH (4 mL) and water (1 mL) was degassed by evacuation and back-filling with argon. XPhos (2-(dicyclohexyl-phosphino)-2',4',6'-tri-i-propyl-1,1'-biphenyl, available from Strem Chemicals; 21.5 mg, 45 μmol) and bis(dibenzylideneacetone)palladium(0) (available from Strem Chemicals; 12.1 mg, 21 μmol) were added. The mixture was degassed again and then heated at 115° C. for 3 h. Water (35 mL) and EtOAc (35 mL) were added. The EtOAc layer was washed with brine (35 mL) and the brine layer was back-extracted with EtOAc (2×30 mL). The combined organic layers were dried (Na$_2$SO$_4$), filtered, and evaporated. The residue was purified by chromatography (50-70% EtOAc/hexanes) to give 6-tert-butyl-2-[3-(5-{5-[2-(3,3-difluoro-azetidin-1-yl)-1,1-dimethyl-ethoxy]-pyridin-2-ylamino}-1-methyl-6-oxo-1,6-dihydro-pyridazin-3-yl)-2-hydroxymethyl-phenyl]-2H-phthalazin-1-one (130 mg, 65%) as a white solid. LC/MS observed [M+H]$^+$ 672.0.

argon. Palladium(II) acetate (10.4 mg, 46 μmol) was added and the mixture was degassed again. The mixture was heated under argon at 100° C. for 16 min. The reaction mixture was filtered through a plug of celite using argon pressure (washing the celite with an additional 2.5 mL of dioxane) to give SOLUTION A.

SOLUTION B was prepared as follows: A mixture of 2-[2-(3-bromo-2-formyl-phenyl)-1-oxo-1,2,3,4-tetrahydro-isoquinolin-6-yl]-2-methyl-propionitrile (which may be prepared as described in Berthel, S. J. et al. US20100222325 Example 153; 166 mg, 0.42 mmol), tricyclohexylphosphine (36 mg, 128 μmol), K2CO3 (290 mg, 2.1 mmol), n-BuOH (534 μL), water (2.1 mL), and dioxane (2.22 mL) was degassed. Bis(dibenzylideneacetone)palladium(0) (36.1 mg, 63 μmol) was added at room temperature. The mixture was vacuum degassed again, and then heated in a heating bath set to 110° C.

SOLUTION A was added to SOLUTION B and the resulting mixture was stirred for 60 min at 110° C. The heating was turned off and the reaction mixture was allowed to stir overnight. The reaction mixture was filtered through celite and the celite was washed with EtOAc. EtOAc (30 mL) and water (30 mL) were added to the filtrate and the EtOAc phase was collected. The aqueous layer was back-extracted with EtOAc (2×20 mL) and the combined organic layers were dried (Na$_2$SO$_4$), filtered, and evaporated. The residue was purified by chromatography using an Analogix system with an SF25-24 g column (eluting with 2-13% MeOH/CH$_2$Cl$_2$) to give 2-(2-{2-formyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-1-oxo-1,2,3,4-tetrahydro-isoquinolin-6-yl)-2-methyl-propionitrile (158 mg, 61%) as a light brown semi-solid. LC/MS observed [M+H]$^+$616.0.

Example 15

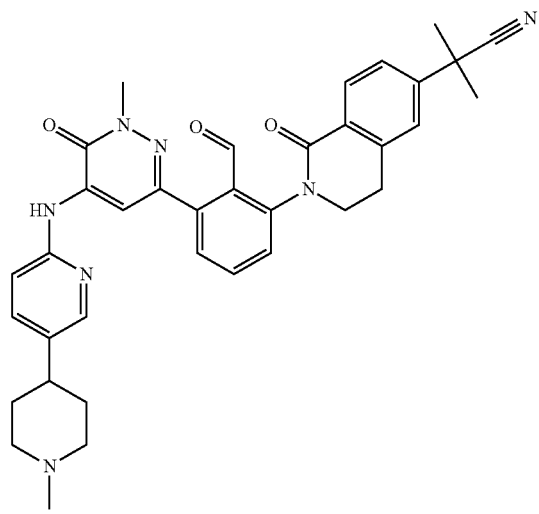 [SMILES: CN1CCC(c2ccc(Nc3cc(-c4cccc(N5CCc6cc(C(C)(C)C#N)ccc6C5=O)c4C=O)nn(C)c3=O)nc2)CC1]

2-(2-{2-Formyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-1-oxo-1,2,3,4-tetrahydro-isoquinolin-6-yl)-2-methyl-propionitrile A mixture of 6-chloro-2-methyl-4-(5-(1-methylpiperidin-4-yl)pyridin-2-ylamino)pyridazin-3(2H)-one (which may be made as described in Berthel, S. J. et al. US20120040949 Preparation of I-67 Step 2; 140 mg, 0.42 mmol), XPhos (2-(dicyclohexylphosphino)-2',4',6'-tri-i-propyl-1,1'-biphenyl, Strem Chemicals; 30 mg, 63 μmol), potassium acetate (123 mg, 1.26 mmol), bis(pinacolato)diboron (Matrix Scientific; 138 mg, 0.55 mmol), and dioxane (7 mL) was degassed by evacuation following by back-filling with

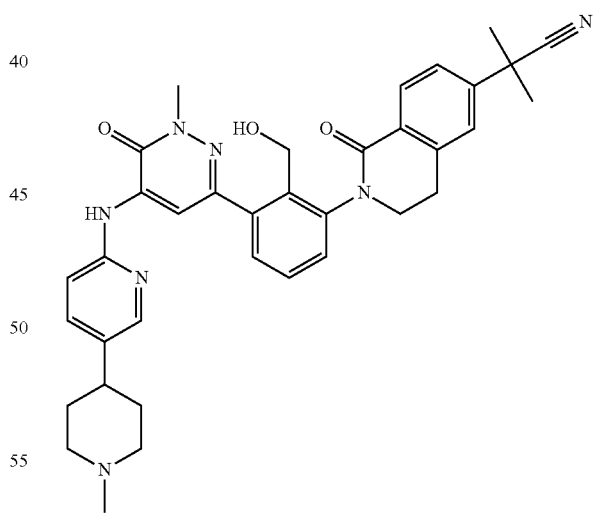

2-(2-{2-Hydroxymethyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-1-oxo-1,2,3,4-tetrahydro-isoquinolin-6-yl)-2-methyl-propionitrile A solution of NaBH$_4$ (49 mg, 1.3 mmol) in water (0.75 mL) was added to a cooled (−0° C.) mixture of 2-(2-{2- formyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-1-oxo-1,2,3,4-tetrahydro-isoquinolin-6-yl)-2-methyl-propionitrile (158 mg, 0.26 mmol), $CH_2Cl_2$ (2 mL) and MeOH (2 mL). The mixture was stirred for 10 min. A solution of $NaBH_4$ (49 mg, 1.3 mmol) in water (0.75 mL) was added and the mixture was stirred for 10 min. A solution of NaBH4 (66 mg, 1.7 mmol) in water (0.75 mL) was added and the mixture was stirred for 5 min. The upper aqueous layer was removed and MeOH (1 mL) was added. Two additional portions of $NaBH_4$ (66 mg, 1.7 mL) in water (0.75 mL) were added at 10 minute intervals, and the reaction mixture was stirred for 10 min. Water (60 mL) and $CH_2Cl_2$ (50 mL) were added. The mixture was shaken in a separatory funnel and the organic layer separated off. The organic layer was washed with 50% aqueous brine (50 mL) and the combined aqueous phases were back-extracted with $CH_2Cl_2$ (2×40 mL). The combined organic layers were dried ($MgSO_4$), filtered and evaporated. The residue was purified using an Analogix purification system with an SF15-12G column (eluting with 1-16% MeOH/CH2Cl2) to give an off-white solid (101 mg). This was recrystallized from $CH_2Cl_2$/hexanes to give 2-(2-{2-hydroxymethyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-1-oxo-1,2,3,4-tetrahydro-isoquinolin-6-yl)-2-methyl-propionitrile (81 mg, 92%) as an off-white powder. LC/MS observed $[M+H]^+$ 618.2.

Biological Examples

Bruton's Tyrosine Kinase (Btk) Inhibition Assay

The assay is a capture of radioactive $^{33}P$ phosphorylated product through filtration. The interactions of Btk, biotinylated $SH_2$ peptide substrate (Src homology), and ATP lead to phosphorylation of the peptide substrate. Biotinylated product is bound streptavidin sepharose beads. All bound, radiolabeled products are detected by scintillation counter.

Plates assayed are 96-well polypropylene (Greiner) and 96-well 1.2 μm hydrophilic PVDF filter plates (Millipore). Concentrations reported here are final assay concentrations: 10-100 μM compounds in DMSO (Burdick and Jackson), 5-10 nM Btk enzyme (His-tagged, full-length), 30 μM peptide substrate (Biotin-Aca-AAAEEIYGEI-NH$_2$), 100 μM ATP (Sigma), 8 mM imidazole (Sigma, pH 7.2), 8 mM glycerol-2-phosphate (Sigma), 200 μM EGTA (Roche Diagnostics), 1 mM $MnCl_2$ (Sigma), 20 mM $MgCl_2$ (Sigma), 0.1 mg/ml BSA (Sigma), 2 mM DTT (Sigma), 1 μCi $^{33}P$ ATP (Amersham), 20% streptavidin sepharose beads (Amersham), 50 mM EDTA (Gibco), 2 M NaCl (Gibco), 2 M NaCl w/1% phosphoric acid (Gibco), microscint-20 (Perkin Elmer).

$IC_{50}$ determinations are calculated from 10 data points per compound utilizing data produced from a standard 96-well plate assay template. One control compound and seven unknown inhibitors were tested on each plate and each plate was run twice. Typically, compounds were diluted in half-log starting at 100 μM and ending at 3 nM. The control compound was staurosporine. Background was counted in the absence of peptide substrate. Total activity was determined in the presence of peptide substrate. The following protocol was used to determine Btk inhibition.
1) Sample preparation: The test compounds were diluted at half-log increments in assay buffer (imidazole, glycerol-2-phosphate, EGTA, $MnCl_2$, $MgCl_2$, BSA).

2) Bead preparation
   a.) rinse beads by centrifuging at 500 g
   b.) reconstitute the beads with PBS and EDTA to produce a 20% bead slurry
3) Pre-incubate reaction mix without substrate (assay buffer, DTT, ATP, $^{33}P$ ATP) and mix with substrate (assay buffer, DTT, ATP, $^{33}P$ ATP, peptide substrate) 30° C. for 15 min.
4) To start assay, pre-incubate 10 μL Btk in enzyme buffer (imidazole, glycerol-2-phosphate, BSA) and 10 L of test compounds for 10 min at RT.
5) Add 30 μL reaction mixture without or with substrate to Btk and compounds.
6) Incubate 50 μL total assay mix for 30 min at 30° C.
7) Transfer 40 μL of assay to 150 μL bead slurry in filter plate to stop reaction.
8) Wash filter plate after 30 min, with following steps
   a. 3×250 μL NaCl
   b. 3×250 μL NaCl containing 1% phosphoric acid
   c. 1×250 μL $H_2O$
9) Dry plate for 1 h at 65° C. or overnight at RT
10) Add 50 μL microscint-20 and count $^{33}P$ cpm on scintillation counter.

Calculate percent activity from raw data in cpm percent activity=(sample−bkg)/(total activity−bkg)×100

Calculate $IC_{50}$ from percent activity, using one-site dose response sigmoidal model $y=A+((B-A)/(1+((x/C)^D))))$ x=cmpd conc, y=% activity, A=min, B=max, C=$IC_{50}$, D=1 (hill slope)

Inhibition of B Cell Activation in Whole Blood Measured by CD69 Expression

A procedure to test the ability of Btk inhibitors to suppress B cell receptor-mediated activation of B cells in human blood is as follows:

Human whole blood (HWB) is obtained from healthy volunteers, with the following restrictions: 24 hr drug-free, non-smokers. Blood is collected by venipuncture into Vacutainer tubes anticoagulated with sodium heparin. Test compounds are diluted to ten times the desired starting drug concentration in PBS (20×), followed by three-fold serial dilutions in 10% DMSO in PBS to produce a nine point dose-response curve. 5.5 μl of each compound dilution is added in duplicate to a 2 ml 96-well V bottom plate (Analytical Sales and Services, #59623-23); 5.5 μl of 10% DMSO in PBS is added to control and no-stimulus wells. HWB (100 μl) is added to each well, and after mixing the plates are incubated at 37 C, 5% $CO_2$, 100% humidity for 30 minutes. Goat F(ab')2 anti-human IgM (Southern Biotech, #2022-14) (10 μl of a 500 μg/ml solution, 50 μg/ml final concentration) is added to each well (except the no-stimulus wells) with mixing and the plates are incubated for an additional 20 hours.

At the end of the 20 hour incubation, samples are incubated with florescent-probe-labeled antibodies (15 μl PE Mouse anti-Human CD20, BD Pharmingen, #555623, and/or 20 ul APC Mouse anti-Human CD69, BD Pharmingen #555533) for 30 minutes, at 37 C, 5% $CO_2$, 100% humidity. Included are induced control, unstained and single stains for compensation adjustments and initial voltage settings. Samples are then lysed with 1 ml of 1× Pharmingen Lyse Buffer (BD Pharmingen #555899), and plates are centrifuged at 1800 rpm for 5 minutes. Supernatants are removed via suction and the remaining pellets are lysed again with another 1 ml of 1× Pharmingen Lyse Buffer, and plates are spun down as before. Supernatants are aspirated and remaining pellets are washed in FACs buffer (PBS+1% FBS). After a final spin, the supernatants are removed and pellets are resuspended in 180 μl of FACs buffer. Samples are transferred to a 96 well plate suitable to be run on the HTS 96 well system on the BD LSR II flow cytometer.

Using appropriate excitation and emission wavelengths for the fluorophores used, data are acquired and percent positive cell values are obtained using Cell Quest Software. Results are initially analyzed by FACS analysis software (Flow Jo). The IC50 for test compounds is defined as the concentration which decreases by 50% the percentage of CD69-positive cells that are also CD20-positive after stimulation by anti-IgM (average of 8 control wells, after subtraction of the average of 8 wells for the no-stimulus background). The IC50 values are calculated using XLfit software version 3, equation 201.

Representative compound data for this assay are listed below in Table II.

TABLE II

| Compound | Human Whole Blood IC50 (μM) |
|---|---|
| I-1 | 0.006 |
| I-2 | 0.01 |
| I-3 | 0.03 |
| I-4 | 0.032 |
| I-5 | 0.035 |
| I-6 | 0.036 |
| I-7 | 0.038 |
| I-8 | 0.042 |
| I-9 | 0.045 |
| I-10 | 0.047 |
| I-11 | 0.135 |
| I-12 | 0.187 |
| I-13 | 0.188 |
| I-14 | 0.573 |
| I-15 | 0.198 |

Inhibition of B-cell Activation

B Cell FLIPR Assay in Ramos Cells

Inhibition of B-cell activation by compounds of the present invention is demonstrated by determining the effect of the test compounds on anti-IgM stimulated B cell responses.

The B cell FLIPR assay is a cell based functional method of determining the effect of potential inhibitors of the intracellular calcium increase from stimulation by an anti-IgM antibody. Ramos cells (human Burkitt's lymphoma cell line. ATCC-No. CRL-1596) were cultivated in Growth Media (described below). One day prior to assay, Ramos cells were resuspended in fresh growth media (same as above) and set at a concentration of $0.5 \times 10^6$/mL in tissue culture flasks. On day of assay, cells are counted and set at a concentration of $1 \times 10^6$/mL1 in growth media supplemented with 1 μM FLUO-3AM(TefLabs Cat-No. 0116, prepared in anhydrous DMSO and 10% Pluronic acid) in a tissue culture flask, and incubated at 37° C. (4% $CO_2$) for one h. To remove extracellular dye, cells were collected by centrifugation (5 min, 1000 rpm), resuspended in FLIPR buffer (described below) at $1 \times 10^6$ cells/mL and then dispensed into 96-well poly-D-lysine coated black/clear plates (BD Cat-No. 356692) at $1 \times 10^5$ cells per well. Test compounds were added at various concentrations ranging from 100 μM to 0.03 μM (7 concentrations, details below), and allowed to incubate with cells for 30 min at RT. Ramos cell $Ca^{2+}$ signaling was stimulated by the addition of 10 μg/mL anti-IgM (Southern Biotech, Cat-No. 2020-01) and measured on a FLIPR (Molecular Devices, captures images of 96 well plates using a CCD camera with an argon laser at 480 nM excitation).

Media/Buffers:

Growth Medium: RPMI 1640 medium with L-glutamine (Invitrogen, Cat-No. 61870-010), 10% Fetal Bovine Serum (FBS, Summit Biotechnology Cat-No. FP-100-05); 1 mM Sodium Pyruvate (Invitrogen Cat. No. 11360-070).

FLIPR buffer: HBSS (Invitrogen, Cat-No. 141175-079), 2 mM $CaCl_2$ (Sigma Cat-No. C-4901), HEPES (Invitrogen, Cat-No. 15630-080), 2.5 mM Probenecid (Sigma, Cat-No. P-8761), 0.1% BSA (Sigma, Cat-No. A-7906), 11 mM Glucose (Sigma, Cat-No. G-7528)

Compound Dilution Details:

In order to achieve the highest final assay concentration of 100 μM, 24 μL of 10 mM compound stock solution (made in DMSO) is added directly to 576 μL of FLIPR buffer. The test compounds are diluted in FLIPR Buffer (using Biomek 2000 robotic pipettor) resulting in the following dilution scheme: vehicle, $1.00 \times 10^{-4}$ M, $1.00 \times 10^{-5}$, $3.16 \times 10^{-6}$, $1.00 \times 10^{-6}$, $3.16 \times 10^{-7}$, $1.00 \times 10^{-7}$, $3.16 \times 10^{-8}$.

Assay and Analysis:

Intracellular increases in calcium were reported using a max-min statistic (subtracting the resting baseline from the peak caused by addition of the stimulatory antibody using a Molecular Devices FLIPR control and statistic exporting software. The $IC_{50}$ was determined using a non-linear curve fit (GraphPad Prism software).

Mouse Collagen-Induced Arthritis (mCIA)

On day 0 mice are injected at the base of the tail or several spots on the back with an emulsion of Type II Collagen (i.d.) in Complete Freund's adjuvant (CFA). Following collagen immunization, animals will develop arthritis at around 21 to 35 days. The onset of arthritis is synchronized (boosted) by systemic administration of collagen in Incomplete Freund's adjuvant (IFA; i.d.) at day 21. Animals are examined daily after day 20 for any onset of mild arthritis (score of 1 or 2; see score description below) which is the signal to boost. Following boost, mice are scored and dosed with candidate therapeutic agents for the prescribed time (typically 2-3 weeks) and dosing frequency, daily (QD) or twice-daily (BID).

Rat Collagen-Induced Arthritis (rCIA)

On day 0, rats are injected with an emulsion of Bovine Type II Collagen in Incomplete Freund's adjuvant (IFA) is injected intradermally (i.d.) on several locations on the back. A booster injection of collagen emulsion is given around day 7, (i.d.) at the base of the tail or alternative sites on the back. Arthritis is generally observed 12-14 days after the initial collagen injection. Animals may be evaluated for the development of arthritis as described below (Evaluation of arthritis) from day 14 onwards. Animals are dosed with candidate therapeutic agents in a preventive fashion starting at the time of secondary challenge and for the prescribed time (typically 2-3 weeks) and dosing frequency, daily (QD) or twice-daily (BID).

Evaluation of Arthritis:

In both models, developing inflammation of the paws and limb joints is quantified using a scoring system that involves the assessment of the 4 paws following the criteria described below:

Scoring: 1=swelling and/or redness of paw or one digit.
2=swelling in two or more joints.
3=gross swelling of the paw with more than two joints involved.
4=severe arthritis of the entire paw and digits.

Evaluations are made on day 0 for baseline measurement and starting again at the first signs or swelling for up to three times per week until the end of the experiment. The arthritic index for each mouse is obtained by adding the four scores of the individual paws, giving a maximum score of 16 per animal.

Rat In Vivo Asthma Model

Male Brown-Norway rats are sensitized i.p. with 100 μg of OA (ovalbumin) in 0.2 ml alum once every week for three weeks (day 0, 7, and 14). On day 21 (one week following last sensitization), the rats are dosed q.d. with either vehicle or compound formulation subcutaneously 0.5 hour before OA aerosol challenge (1% OA for 45 minutes) and terminated 4 or 24 hours after challenge. At time of sacrifice, serum and plasma are collected from all animals for serology and PK, respectively. A tracheal cannula is inserted and the lungs are lavaged 3× with PBS. The BAL fluid is analyzed for total leukocyte number and differential leukocyte counts. Total leukocyte number in an aliquot of the cells (20-100 μl) is determined by Coulter Counter. For differential leukocyte counts, 50-200 μl of the sample is centrifuged in a Cytospin and the slide stained with Diff-Quik. The proportions of monocytes, eosinophils, neutrophils and lymphocytes are counted under light microscopy using standard morphological criteria and expressed as a percentage. Representative inhibitors of Btk show decreased total leucocyte count in the BAL of OA sensitized and challenged rats as compared to control levels.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

The invention claimed is:
1. A compound of Formula I,

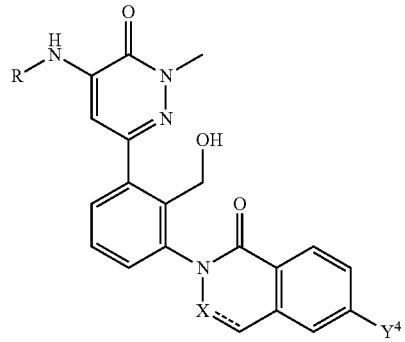

wherein:
═ is either a single or double bond;
X is either CH, CH$_2$, or N;
R is H, —R$^1$, —R$^1$—R$^2$—R$^3$, —R$^1$—R$^3$, or —R$^2$—R$^3$;
R$^1$ is aryl, heteroaryl, bicyclic heteroaryl, cycloalkyl, or heterocycloalkyl, each of which is optionally substituted with one or more lower alkyl, hydroxy, hydroxy lower alkyl, lower alkoxy, halo, nitro, amino, amido, cyano, oxo, or lower haloalkyl;
R$^2$ is —C(═O), —C(═O)O, —C(═O)NR$^{2'}$, —NHC(═O)O, —C(R$^{2'}$)$_2$, —O, —S, —C(═NH)NR$^{2'}$, or —S(═O)$_2$;
each R$^{2'}$ is independently H or lower alkyl;
R$^3$ is H or R$^4$;
R$^4$ is lower alkyl, lower haloalkyl, lower alkoxy, amino, lower alkyl amino, cycloalkyl amino, lower dialkyl amino, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, heterocycloalkyl alkyl, bicyclic cycloalkyl, bicyclic heterocycloalkyl, spirocycloalkyl, spiroheterocycloalkyl, or bicyclic spiroheterocycloalkyl, each of which is optionally substituted with one or more lower alkyl, halo, lower alkyl amino, lower dialkyl amino, hydroxy, hydroxy lower alkyl, lower alkoxy, lower alkanoyl, halo, nitro, amino, amido, acyl, cyano, oxo, sulfonyl, lower alkyl sulfonyl, guanidino, hydroxyl amino, carboxy, carbamoyl, carbamate, halo lower alkoxy, heterocycloalkyl, or halo lower alkyl, wherein two lower alkyl groups may together form a ring;
Y$^4$ is Y$^{4a}$; Y$^{4b}$; Y$^{4c}$, or Y$^{4d}$;
Y$^{4a}$ is H or halogen;
Y$^{4b}$ is lower alkyl, optionally substituted with one or more substituents selected from the group consisting of lower haloalkyl, halogen, hydroxy, amino, cyano, and lower alkoxy;
Y$^{4c}$ is lower cycloalkyl, optionally substituted with one or more substituents selected from the group consisting of lower alkyl, lower haloalkyl, halogen, hydroxy, amino, cyano, and lower alkoxy; and
Y$^{4d}$ is amino, optionally substituted with one or more lower alkyl, alkoxy lower alkyl, or hydroxy lower alkyl;
or a pharmaceutically acceptable salt thereof.
2. The compound of claim 1, wherein ═ is a double bond and X is N.

3. The compound of claim 1, wherein ═ is a single bond and X is CH$_2$.

4. The compound of claim 1, wherein
R is —R$^1$—R$^2$—R$^3$;
R$^1$ is pyridyl;
R$^2$ is —S(═O)$_2$,
R$^3$ is R$^4$; and
R$^4$ is lower alkyl.

5. The compound of claim 1, wherein
R is —R$^1$—R$^2$—R$^3$;
R$^1$ is pyridyl;
R$^2$ is —C(CH$_3$)$_2$;
R$^3$ is R$^4$; and
R$^4$ is lower alkyl amino, lower dialkyl amino, or heterocycloalkyl optionally substituted with one or more lower alkyl.

6. The compound of claim 1, wherein
R is —R$^1$—R$^2$—R$^3$;
R$^1$ is phenyl or pyridyl;
R$^2$ is —C(═O);
R$^3$ is R$^4$; and
R$^4$ is morpholine or piperazine, optionally substituted with one or more lower alkyl.

7. The compound of claim 2, wherein Y$^4$ is tert-butyl.

8. The compound of claim 3, wherein ═ is a double bond, X is CH, and Y$^4$ is

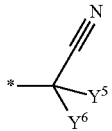

wherein, Y$^5$ and Y$^6$ are independently H, lower alkyl, or lower haloalkyl.

9. The compound of claim 2, wherein Y$^4$ is

wherein, Y$^5$ is H, halogen, lower alkyl or lower haloalkyl.

10. The compound of claim 2, wherein Y$^4$ is

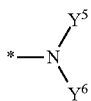

wherein, Y$^5$ and Y$^6$ are independently H or lower alkyl.

11. The compound of claim 7, wherein
R is —R$^1$—R$^3$;
R$^1$ is pyridyl or pyrazolopyrazine;
R$^3$ is R$^4$; and
R$^4$ is optionally substituted lower alkyl, heterocycloalkyl, or alkyl heterocycloalkyl.

12. The compound of claim 7, wherein
R is —R$^1$—R$^2$—R$^3$;
R$^1$ is pyridyl;
R$^2$ is —C(CH$_3$)$_2$;
R$^3$ is R$^4$; and
R$^4$ is lower alkyl amino, lower dialkyl amino, or heterocycloalkyl optionally substituted with one or more lower alkyl.

13. The compound of claim 7, wherein
R is —R$^1$—R$^2$—R$^3$;
R$^1$ is pyridyl;
R$^2$ is —C(═O);
R$^3$ is R$^4$; and
R$^4$ is optionally substituted heterocycloalkyl or bicyclic spiroheterocycloalkyl.

14. The compound of claim 13, wherein R$^4$ is optionally substituted morpholine or piperazine.

15. The compound of claim 1 selected from the group consisting of:
2-(3-{5-[5-(2-Azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-6-tert-butyl-2H-phthalazin-1-one;

6-tert-Butyl-2-{2-hydroxymethyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-2H-phthalazin-1-one;

2-{3-[5-(5-Azetidin-1-ylmethyl-1-methyl-1H-pyrazol-3-ylamino)-1-methyl-6-oxo-1,6-dihydro-pyridazin-3-yl]-2-hydroxymethyl-phenyl}-6-tert-butyl-2H-phthalazin-1-one;

6-tert-Butyl-2-(2-hydroxymethyl-3-{1-methyl-5-[5-((S)-1-methyl-pyrrolidin-2-yl)-pyridin-2-ylamino]-6-oxo-1,6-dihydro-pyridazin-3-yl}-phenyl)-2H-phthalazin-1-one;

6-tert-Butyl-2-(2-hydroxymethyl-3-{1-methyl-5-[5-((S)-1-methyl-pyrrolidin-3-yl)-pyridin-2-ylamino]-6-oxo-1,6-dihydro-pyridazin-3-yl}-phenyl)-2H-phthalazin-1-one;

6-tert-Butyl-2-(2-hydroxymethyl-3-{1-methyl-5-[5-((R)-1-methyl-pyrrolidin-3-yl)-pyridin-2-ylamino]-6-oxo-1,6-dihydro-pyridazin-3-yl}-phenyl)-2H-phthalazin-1-one;

2-(2-{2-Hydroxymethyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-1-oxo-1,2-dihydro-phthalazin-6-yl)-2-methyl-propionitrile;

6-tert-Butyl-2-{2-hydroxymethyl-3-[1-methyl-5-(5-methyl-4,5,6,7-tetrahydro-pyrazolo[1,5-c]pyrazin-2-ylamino)-6-oxo-1,6-dihydro-pyridazin-3-yl]-phenyl}-2H-phthalazin-1-one;

6-tert-Butyl-2-{3-[5-(1'-ethyl-1',2',3',4',5',6'-hexahydro-[3,4']bipyridinyl-6-ylamino)-1-methyl-6-oxo-1,6-dihydro-pyridazin-3-yl]-2-hydroxymethyl-phenyl}-2H-phthalazin-1-one;

6-tert-Butyl-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-2H-phthalazin-1-one;

2-[2-(3-{5-[5-(2-Azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-1-oxo-1,2-dihydro-phthalazin-6-yl]-2-methyl-propionitrile;

6-tert-Butyl-2-[2-hydroxymethyl-3-(5-{5-[2-(3-hydroxy-propylamino)-1,1-dimethyl-ethoxy]-pyridin-2-ylamino}-1-methyl-6-oxo-1,6-dihydro-pyridazin-3-yl)-phenyl]-2H-phthalazin-1-one;

6-tert-Butyl-2-{2-hydroxymethyl-3-[1-methyl-5-(1'-oxetan-3-yl-1',2',3',4',5',6'-hexahydro-[3,4']bipyridinyl-6-ylamino)-6-oxo-1,6-dihydro-pyridazin-3-yl]-phenyl}-2H-phthalazin-1-one;

6-tert-Butyl-2-[3-(5-{5-[2-(3,3-difluoro-azetidin-1-yl)-1,1-dimethyl-ethoxy]-pyridin-2-ylamino}-1-methyl-6-oxo-1,6-dihydro-pyridazin-3-yl)-2-hydroxymethyl-phenyl]-2H-phthalazin-1-one; and 2-(2-{2-Hydroxymethyl-3-[1-methyl-5-(1'-methyl-1',2',3',5',6'-hexahydro-[3,4']bipyridinyl-6-ylamino)-6-oxo-1,6-dihydro-pyridazin-3-yl]-phenyl}-1-oxo-1,2,3,4-tetrahydro-isoquinolin-6-yl)-2-methyl-propionitrile.

16. A method for treating asthma or rheumatoid arthritis, comprising the step of administering to a patient in need thereof a therapeutically effective amount of the compound of claim 1.

17. A pharmaceutical composition comprising the compound of claim 1, admixed with at least one pharmaceutically acceptable carrier, excipient or diluent.

* * * * *